US012721787B2

(12) United States Patent
Pompe et al.

(10) Patent No.: US 12,721,787 B2
(45) Date of Patent: Sep. 1, 2026

(54) SYSTEMS AND APPROACHES FOR DRUG DELIVERY

(71) Applicants: AMGEN INC., Thousand Oaks, CA (US); AMGEN RESEARCH MUNICH GMBH, Munich (DE)

(72) Inventors: Cornelius Pompe, Munich (DE); Nicholas J. Clark, Thousand Oaks, CA (US); Wei Qi, Thousand Oaks, CA (US); Arnold J. McAuley, Thousand Oaks, CA (US); Michael Schneider, Thousand Oaks, CA (US); Chia-Jung Wu, Redondo Beach, CA (US); Twinkle R. Christian, Thousand Oaks, CA (US); Heather N. Franey, Ventura, CA (US); Bharadwaj Jagannathan, Thousand Oaks, CA (US); Jeffrey Abel, Thousand Oaks, CA (US); Franz Dietzel, Munich (DE)

(73) Assignees: AMGEN INC., Thousand Oaks, CA (US); AMGEN RESEARCH MUNICH GMBH, Munich (DE)

( * ) Notice: Subject to any disclaimer, the term of this patent is extended or adjusted under 35 U.S.C. 154(b) by 1162 days.

(21) Appl. No.: 17/770,355

(22) PCT Filed: Oct. 23, 2020

(86) PCT No.: PCT/US2020/057054

§ 371 (c)(1),
(2) Date: Apr. 20, 2022

(87) PCT Pub. No.: WO2021/081321

PCT Pub. Date: Apr. 29, 2021

(65) Prior Publication Data

US 2022/0362104 A1 Nov. 17, 2022

Related U.S. Application Data

(60) Provisional application No. 62/925,685, filed on Oct. 24, 2019.

(51) Int. Cl.
*G01N 21/64* (2006.01)
*A61J 1/14* (2023.01)
(Continued)

(52) U.S. Cl.
CPC .......... *A61J 1/1468* (2015.05); *A61M 5/1413* (2013.01); *G01N 33/15* (2013.01); *A61M 2205/702* (2013.01); *A61M 2209/02* (2013.01)

(58) Field of Classification Search
CPC ................ A61J 1/1468; A61M 5/1413; A61M 2205/702; A61M 2209/02; A61M 5/14212; G01N 33/15; A61P 35/00
See application file for complete search history.

(56) References Cited

U.S. PATENT DOCUMENTS 5,022,972 A * 6/1991 David .................. G01N 27/447 204/549
8,439,889 B2 5/2013 Sano
(Continued)

FOREIGN PATENT DOCUMENTS

CN 104403122 A 3/2015
JP H0444771 A 2/1992
(Continued)

OTHER PUBLICATIONS

DePalma, V. A. "Apparatus for zeta potential measurement of rectangular flow cells." Review of Scientific Instruments 51.10 (1980): 1390-1395. (Year: 1980).*
(Continued)

*Primary Examiner* — Jennifer Wecker
*Assistant Examiner* — Oyeleye Alexander Alabi
(74) *Attorney, Agent, or Firm* — MARSHALL, GERSTEIN & BORUN LLP

(57) ABSTRACT

An approach for determining material compatibility for components of a drug delivery system is provided that includes using surface zeta-potential analytical method to
(Continued)

evaluate surface interactions between a desired molecule and at least one material present within a given IV-bag system.

4 Claims, 26 Drawing Sheets

Specification includes a Sequence Listing.

(51) Int. Cl.

| | |
|---|---|
| ***A61M 5/14*** | (2006.01) |
| ***C07F 5/02*** | (2006.01) |
| ***C09B 57/00*** | (2006.01) |
| ***C09K 11/06*** | (2006.01) |
| ***G01N 15/10*** | (2024.01) |
| ***G01N 15/1429*** | (2024.01) |
| ***G01N 27/626*** | (2021.01) |
| ***G01N 31/22*** | (2006.01) |
| ***G01N 33/15*** | (2006.01) |
| ***G01N 33/483*** | (2006.01) |
| ***G01N 33/68*** | (2006.01) |

(56) References Cited

U.S. PATENT DOCUMENTS 9,629,955 B2 * 4/2017 Bresina ................. A61M 5/142
2005/0113579 A1 * 5/2005 Brown ................. C07D 221/14 546/98
2010/0216667 A1 * 8/2010 Meyer .................... G01N 24/08 204/452

FOREIGN PATENT DOCUMENTS

JP 2013138920 A 7/2013
JP 2017505815 A 2/2017
JP 2017529313 A 10/2017
JP 2018-188437 A 11/2018
WO WO-8803265 A1 5/1988
WO WO-2015114593 A2 8/2015
WO WO-2016019627 A1 2/2016
WO WO-2018129331 A1 * 7/2018 ........... C07K 16/468
WO WO-2018204907 A1 11/2018

OTHER PUBLICATIONS

Ferraris, Sara, et al. "Zeta potential measurements on solid surfaces for in vitro biomaterials testing: surface charge, reactivity upon contact with fluids and protein absorption." Frontiers in bioengineering and biotechnology 6 (2018): 60. (Year: 2018).*

Bhattacharjee, Sourav. "DLS and zeta potential—what they are and what they are not?." Journal of controlled release 235 (2016): 337-351. (Year: 2016).*

Written Opinion and International Search Report issued to International Application No. PCT/US2020/057054, dated Mar. 24, 2021.

Bhattacharjee Sourav Ed—Hanes Justin et al: "DLS and zeta potential—What they are and what they are not?", Journal of Controlled Release, Elsevier, Amsterdam, NL, vol. 235, Jun. 10, 2016, pp. 337-351, XP029633356, ISSN: 0168-3659, DOI: 10.1016/J.JCONREL.2016.06.017.

Judy Y Chang et al: "Leachables from Saline-Containing IV Bags Can Alter Therapeutic Protein Properties", Pharmaceutical Research, Kluwer Academic Publishers-Plenum Publishers, N., vol. 27, No. 11, Jun. 30, 2010 , pp. 2402-2413, XP019828025, ISSN: 1573-904X.

Malvern Analytical: "Zetasizer Pro and Zetasizer Ultra Advance With Confidence", Dec. 31, 2018, XP055766681, URL: https://www.malvernpanalytical.com/en/assets/MRK2351-01_Zetasizer_Brochure_LRA4_tcm50-56369.pdf.

* cited by examiner

Top Layer (1x2 cm)
(bag Inner Layer down)

Solution flow path

Bottom Layer (1x2 cm)
(bag Inner Layer up)

100 µm

| ≥ 10 µm | Average Cumulative Counts/Container t = 0 | t = 24 h |
|---|---|---|
| EVA 0.1 µg/mL 2°C to 8°C | 467 | 67 |
| EVA 0.1 µg/mL 25°C | 0 | 67 [a] |
| Polyolefin 0.1 µg/mL 2°C to 8°C | 133 | 267 |
| Polyolefin 0.1 µg/mL 25°C_#1 | 0 | 67 [a] |
| Polyolefin 0.1 µg/mL 25°C_#2 | 733 | 0 [b] |
| Syringe 0.1 µg/mL 2°C to 8°C | 128 | 80 |
| Syringe 0.1 µg/mL 25°C | 128 | 8 [a] |
| EVA 25 µg/mL 2°C to 8°C | 0 | 67 |
| EVA 25 µg/mL 25°C | 133 | 267 [a] |
| Polyolefin 25 µg/mL 2°C to 8°C | 0 | 67 |
| Polyolefin 25 µg/mL 25°C | 133 | 0 [a] |
| EVA 100 µg/mL 2°C to 8°C | 467 | 533 |
| EVA 100 µg/mL 25°C | 1600 | 4067 [a] |
| Polyolefin 100 µg/mL 2°C to 8°C | 467 | 533 |
| Polyolefin 100 µg/mL 25°C_#1 | 200 | 3733 [a] |
| Polyolefin 100 µg/mL 25°C_#2 | 533 | 400 [b] |

| ≥ 25 µm | Average Cumulative Counts/Container t = 0 | t = 24 h |
|---|---|---|
| EVA 0.1 µg/mL 2°C to 8°C | 133 | 0 |
| EVA 0.1 µg/mL 25°C | 0 | 0 [a] |
| Polyolefin 0.1 µg/mL 2°C to 8°C | 0 | 67 |
| Polyolefin 0.1 µg/mL 25°C_#1 | 0 | 67 [a] |
| Polyolefin 0.1 µg/mL 25°C_#2 | 67 | 0 [b] |
| Syringe 0.1 µg/mL 2°C to 8°C | 0 | 0 |
| Syringe 0.1 µg/mL 25°C | 0 | 0 [a] |
| EVA 25 µg/mL 2°C to 8°C | 0 | 0 |
| EVA 25 µg/mL 25°C | 0 | 0 [a] |
| Polyolefin 25 µg/mL 2°C to 8°C | 0 | 0 |
| Polyolefin 25 µg/mL 25°C | 67 | 0 [a] |
| EVA 100 µg/mL 2°C to 8°C | 0 | 67 |
| EVA 100 µg/mL 25°C | 0 | 67 [a] |
| Polyolefin 100 µg/mL 2°C to 8°C | 0 | 67 |
| Polyolefin 100 µg/mL 25°C_#1 | 0 | 67 [a] |
| Polyolefin 100 µg/mL 25°C_#2 | 0 | 0 [b] |

Fig. 9

| Container | HMW (%) t = 0 | HMW (%) t = 24 h |
|---|---|---|
| 25 µg/mL AMG 701 EVA 2°C to 8°C | 0.3 | 0.2 |
| 25 µg/mL AMG 701 EVA 25°C | 0.4 | 0.2[a] |
| 25 µg/mL AMG 701 Polyolefin 2°C to 8°C | 0.6 | 0.2 |
| 25 µg/mL AMG 701 Polyolefin 25°C | 0.5 | 0.2[ab] |
| 100 µg/mL AMG 701 EVA 2°C to 8°C | 0.2 | 0.3 |
| 100 µg/mL AMG 701 EVA 25°C | 0.4 | 0.3 |
| 100 µg/mL AMG 701 Polyolefin 2°C to 8°C | 0.5 | 0.4 |
| 100 µg/mL AMG 701 Polyolefin 25°C_#1 | 0.2 | 0.4[a] |
| 100 µg/mL AMG 701 Polyolefin 25°C_#2 | 0.1 | 0.2[b] |

Sampling occurred through a polyethylene infusion set (with 0.22 um filter) extended with a polyvinyl acetate infusion set prior to analytical testing. b Sampling was performed through polyurethane infusion line. Other samples used a polyethylene infusion set without filter only.

Fig. 10

| | Protein titer [a] (µg/mL) | | | | | | Change [b] (%) |
|---|---|---|---|---|---|---|---|
| Storage time [h] | 0 | 0 | 4 | 4 | 24 | 21 | |
| Infusion time [h] | 0 | 3 | 0 | 3 | 0 | 3 | |
| Total contact time [h] | 0 | 3 | 4 | 7 | 24 | 24 | |
| Infusion rate controlled | no | no | no | yes | no | yes | |
| PE infusion set (w/o filter) | | | | | | | |
| EVA 0.1 µg/mL 2°C to 8°C | 0.096 | - | - | - | 0.097 | - | 1.0 |
| EVA 0.1 µg/mL 25°C #1 | 0.089 | - | - | - | - | - | - |
| EVA 0.1 µg/mL 25°C #2 | 0.100 | - | 0.096 | - | - | - | 4.0 |
| EVA 0.1 µg/mL 25°C #3 | 0.106 | - | - | - | - | - | - |
| EVA 0.1 µg/mL 25°C #4 | 0.086 | - | - | - | - | - | - |
| Polyolefin 0.1 µg/mL 2°C to 8°C | 0.090 | - | - | - | 0.097 | - | 7.8 |
| Polyolefin 0.1 µg/mL 25°C #1 | 0.092 | - | - | - | - | - | - |
| Polyolefin 0.1 µg/mL 25°C #2 | 0.096 | - | 0.094 | - | - | - | 2.1 |
| Polyolefin 0.1 µg/mL 25°C #3 | 0.092 | - | - | - | - | - | - |
| Syringe 0.1 µg/mL 2°C to 8°C | 0.093 | - | - | - | 0.100 | - | 7.5 |
| Syringe 0.1 µg/mL 25°C #1 | 0.093 | - | - | - | - | 0.092 | 1.1 |
| Syringe 0.1 µg/mL 25°C #2 | 0.110 | - | 0.102 | - | - | - | 7.3 |
| Syringe 0.1 µg/mL 25°C #3 | 0.119 | - | - | 0.108 | - | - | 6.7 |
| EVA 25 µg/mL 2°C to 8°C | 24.8 | - | - | - | 24.6 | - | 0.8 |
| EVA 25 µg/mL 25°C | 22.9 | - | - | - | - | - | - |
| Polyolefin 25 µg/mL 2°C to 8°C | 22.4 | - | - | - | 23.6 | - | 5.4 |
| Polyol efin 25 µg/mL 25°C | 21.3 | - | - | - | - | - | - |
| EVA 100 µg/mL 2°C to 8°C | 108.6 | - | - | - | 101.8 | - | 6.3 |
| EVA 100 µg/mL 25°C | 105.5 | - | - | - | - | - | - |
| Polyolefin 100 µg/mL 2°C to 8°C | 109.5 | - | - | - | 101.6 | - | 7.2 |
| Polyolefin 100 µg/mL 25°C | 107.9 | - | - | - | - | - | - |

Fig. 11a

| | Protein titer [a] (µg/mL) | | | | | | Change [b] (%) |
|---|---|---|---|---|---|---|---|
| Storage time [h] | 0 | 0 | 4 | 4 | 24 | 21 | |
| Infusion time [h] | 0 | 3 | 0 | 3 | 0 | 3 | |
| Total contact time [h] | 0 | 3 | 4 | 7 | 24 | 24 | |
| Infusion rate controlled | no | no | no | yes | no | yes | |
| PE infusion set (with filter) | | | | | | | |
| EVA 0.1 µg/mL 25°C #4 | - | 0.087 | - | - | - | - | 1.2 |
| Polyolefin 0.1 µg/mL 25°C #4 | 0.092 | 0.101 | - | - | - | - | 9.8 |
| PE infusion set (with filter) + PVC extension | | | | | | | |
| EVA 0.1 µg/mL 25°C #1 | - | - | - | - | - | 0.076 | -15.1 |
| EVA 0.1 µg/mL 25°C #3 | - | - | - | 0.077 | - | - | -27.3 |
| Polyolefin 0.1 µg/mL 25°C #1 | - | - | - | - | - | 0.067 | -27.2 |
| Polyolefin 0.1 µg/mL 25°C #3 | - | - | - | 0.061 | - | - | -33.7 |
| EVA 25 µg/mL 25°C | - | - | - | - | - | 21.1 | -7.9 |
| Polyolefin 25 µg/mL 25°C | - | - | - | - | - | 20.8 | -2.3 |
| EVA 100 µg/mL 25°C | - | - | - | - | - | 95.7 | -9.3 |
| Polyolefin 100 µg/mL 25°C | - | - | - | - | - | 97.1 | -10.0 |
| PU infusion set (w/o filter) | | | | | | | |
| Polyolefin 0.1 µg/mL 25°C | 0.109 | - | - | - | - | 0.108 | -0.9 |
| Polyolefin 100 µg/mL 25°C | 98.2 | | | | | 104.3 | 6.1 |

Fig. 11b

| | Relative potency (%) * | | |
|---|---|---|---|
| Storage time [h] | 0 | 24 | 21 |
| Infusion time [h] | 0 | 0 | 3 |
| Total contact time [h] | 0 | 24 | 24 |
| Infusion rate controlled | no | no | yes |
| PE infusion set (w/o filter) | | | |
| EVA 25 µg/mL 2°C to 8°C | 79 | 82 | - |
| EVA 25 µg/mL 25°C | 76 | - | - |
| Polyolefin 25 µg/mL 2°C to 8°C | 90 | 89 | - |
| Polyolefin 25 µg/mL 25°C | 100 | - | - |
| EVA 100 µg/mL 2°C to 8°C | 87 | 95 | - |
| EVA 100 µg/mL 25°C | 89 | - | - |
| Polyolefin 100 µg/mL 2°C to 8°C | 88 | 98 | - |
| Polyolefin 100 µg/mL 25°C | 94 | - | - |
| PE infusion set (with filter) + PVC extension | | | |
| EVA 25 µg/mL 25°C | - | - | 80 |
| Polyolefin 25 µg/mL 25°C | - | - | 94 |
| EVA 100 µg/mL 25°C | - | - | 94 |
| Polyolefin 100 µg/mL 25°C | - | - | 96 |

Fig. 12

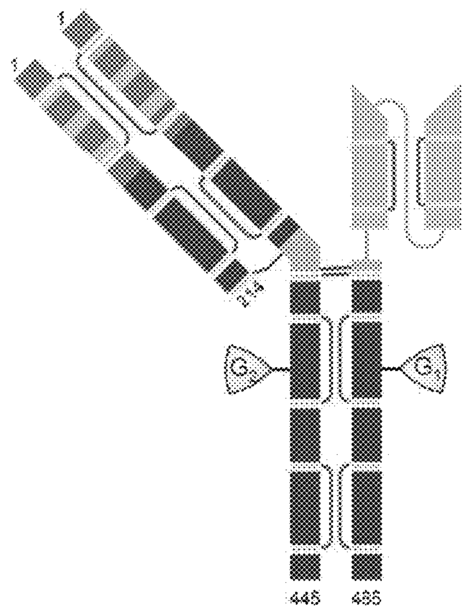

Fig. 13

ScFv-Fc

| | | | | | |
|---|---|---|---|---|---|
| 1 | EVQLVESGGG | LVOPGGSLRL | SCAASGETFS | TYAMNWVROA | PGKGLEWVGR |
| 51 | IRSKANNYAT | YYADSVKGRF | TISRDDSKNT | LYLQMNSLRA | EDTAVYYCVR |
| 101 | HGNFGDSYVS | WFAYWGQGTL | VTVSSGKPGS | GKPGSGKPGS | GKPGSQAVVT |
| 151 | QEPSLTVSPG | GTVTLTCGSS | TGAVTTSNYA | NWVQQKPGKS | PRGLIGGTNK |
| 201 | RAPGVPARFS | GSLLGGKAAL | TISGAQPEDE | ADYYCALWYS | NHWVFGGGTK |
| 251 | LTVLEPKSSD | KTHTCPPCPA | PPVAGPSVFL | FPPKPKDTLM | ISRTPEVTCV |
| 301 | VVDVKHEDPE | VKFNWYVDGV | EVHNAKTKPR | EEQYNSTYRV | VSVLTVLHQD |
| 351 | WLNGKEYKCK | VSNKALPAPI | EKTISKAKGQ | PREPQVYTLP | PSREOMTKNQ |
| 401 | VKLICLVKGE | YPSDIAVEWE | SNGQPENNYK | TTPPVLDSDG | SFFLYSKLTV |
| 451 | DKSRWQOGNV | FSCSVMHEAL | HNHYTQKSLS | LSPGK | |

Heavy Chain

| | | | | | |
|---|---|---|---|---|---|
| 1 | EVQLVESGGG | LVQPGGSLRL | SCAASGFDFS | RSWMNWVROA | PGKGLEWVSE |
| 51 | INPDSSTINY | ATSVKGRFTI | SRDNSKNTLY | LQMNSLRAED | TAVYYCARYG |
| 101 | NWFPYWGQGT | LVTVSSASTK | GPSVEPLAPS | SKSTSGGTAA | LGCLVKDYFP |
| 151 | EPVIVSWNSG | ALTSGVHTFP | AVLQSSGLYS | LSSVVTVPSS | SLGTQTYICN |
| 201 | VNHKPSDTKV | DKKVEPKSCD | KTHTCPPCPA | PFVAGPSVFL | FPPKPRDTLM |
| 251 | ISRTPEVTCV | VVDVKHEDPE | VKENWYVDGV | EVHNAKTKPR | EEEYNSTYRV |
| 301 | VSVLTVLHQD | WLNGKEYKCK | VSNKALPAPI | EKTISKAKGQ | PREPQVYTLP |
| 351 | PSREEMTKNQ | VSLTCDVSGF | YPSDIAVEWE | SDGQPENNYK | TTPPVLDSDG |
| 401 | SFFLYSKLTV | DKSRWEQGDV | FSCSVMHEAL | HNHYTQKSLS | LSPGK |

Light Chain

| | | | | | |
|---|---|---|---|---|---|
| 1 | DIVMTQSPSS | LSASVGDRVT | ITCRASQNVD | TWVAWYQQKP | GQSPKALIYS |
| 51 | ASYRYSGVPD | RFTGSGSGTD | FTLTISSLOP | EDFATYFCOO | YDSYPLTFGG |
| 101 | GTKLEIKRTV | AAPSVFIFPP | SDEQLKSGTA | SVVCLLNNFY | PREAKVQWKV |
| 151 | DNALOSGNSQ | ESVTEQDSKD | STYSLSSTLT | LSKADYEKHK | VYACEVTHOG |
| 201 | LSSPVTKSEN | RGEC | | | |

Fig. 14

| IV Bag Material Type | Concentration of AMG 424 | Temperature | Time |
|---|---|---|---|
| Ethyl vinyl acetate | 1 µg/mL | 2°C to 8°C | 0 and 24 h[a] |
| | | 25°C | 0 and 24 h[a] |
| | 4 mg/mL | 2°C to 8°C | 0 and 24 h[a] |
| | | 25°C | 0 and 24 h[a] |
| Polyolefin | 1 µg/mL | 2°C to 8°C | 0 and 24 h[a] |
| | | 25°C | 0 and 24 h[a] |
| | 4 mg/mL | 2°C to 8°C | 0 and 24 h[a] |
| | | 25°C | 0 and 24 h[a] |

Fig. 15

| Container | t = 0 | t = 24 h[a] |
|---|---|---|
| 1 µg/mL AMG 424 EVA 2°C to 8°C | No Particles | No Particles |
| 1 µg/mL AMG 424 EVA 25°C | No Particles | No Particles |
| 1 µg/mL AMG 424 Polyolefin 2°C to 8°C | No Particles | No Particles |
| 1 µg/mL AMG 424 Polyolefin 25°C | No Particles | No Particles |
| 4 mg/mL AMG 424 EVA 2°C to 8°C | No Particles | No Particles |
| 4 mg/mL AMG 424 EVA 25°C | No Particles | No Particles |
| 4 mg/mL AMG 424 Polyolefin 2°C to 8°C | No Particles | No Particles |
| 4 mg/mL AMG 424 Polyolefin 25°C | No Particles | No Particles |

Fig. 16

| | Average Cumulative Counts/Container | |
|---|---|---|
| 10 micron | t = 0 | t = 24 h[a] |
| 1 μg/mL EVA 2°C to 8°C | 12 | 0 |
| 1 μg/mL EVA 25°C | 22 | 2 |
| 1 μg/mL Polyolefin 2°C to 8°C | 0 | 0 |
| 1 μg/mL Polyolefin 25°C | 0 | 0 |
| 4 mg/mL EVA 2°C to 8°C | 25 | 0 |
| 4 mg/mL EVA 25°C | 100 | 3 |
| 4 mg/mL Polyolefin 2°C to 8°C | 37 | 5 |
| 4 mg/mL Polyolefin 25°C | 93 | 3 |
| 25 micron | t = 0 | t = 24 h[a] |
| 1 μg/mL EVA 2°C to 8°C | 0 | 0 |
| 1 μg/mL EVA 25°C | 0 | 0 |
| 1 μg/mL Polyolefin 2°C to 8°C | 0 | 0 |
| 1 μg/mL Polyolefin 25°C | 0 | 0 |
| 4 mg/mL EVA 2°C to 8°C | 0 | 0 |
| 4 mg/mL EVA 25°C | 3 | 0 |
| 4 mg/mL Polyolefin 2°C to 8°C | 0 | 0 |
| 4 mg/mL Polyolefin 25°C | 0 | 0 |

Fig. 17

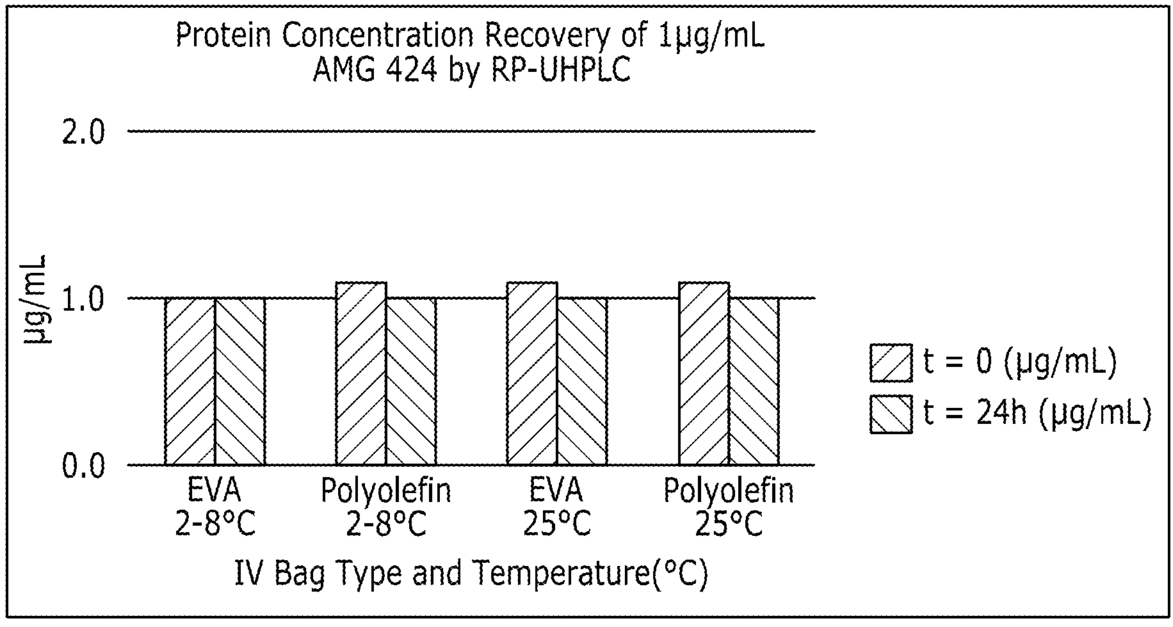
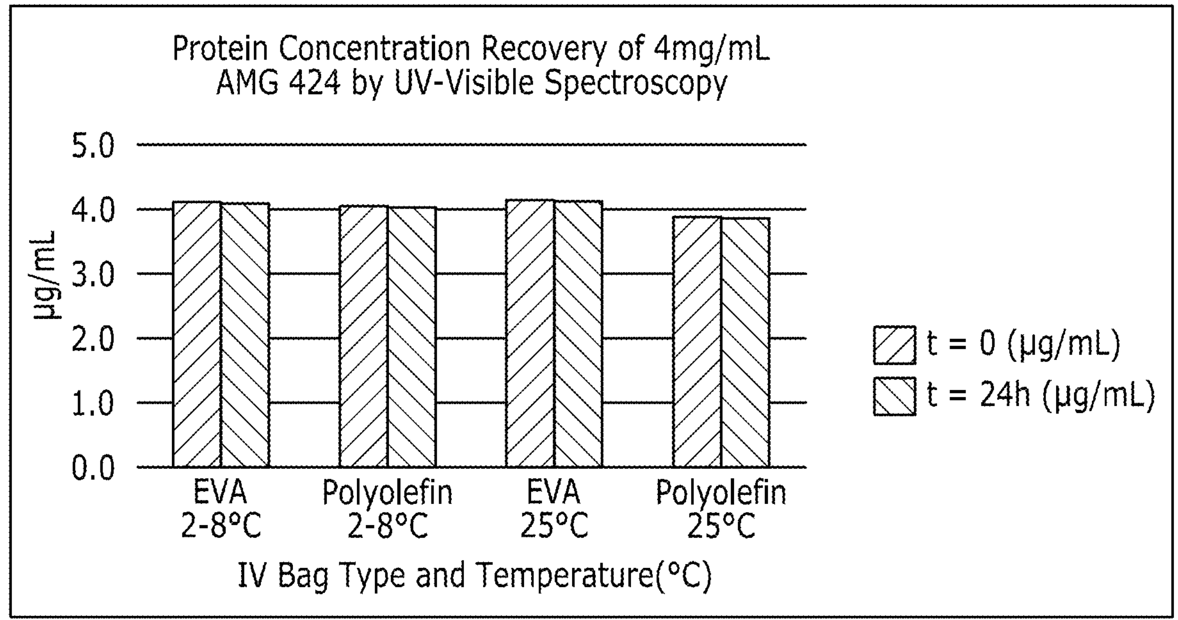
Fig. 18

| Container (nominal volume) | Concentration of AMG 160 (µg/mL) | Contact Time (h) | Temperature (°C) | Infusion Set | Infusion Rate (mL/h) |
|---|---|---|---|---|---|
| EVA IV bag (100 mL) | 0.1 | 0 | 5 | - | - |
| | | 24 | 5 | - | - |
| | | 24 | 25 | - | - |
| | | 24 | 25 | PVC (w/o filter) | 27 |
| | | 24 | 25 | PE (w/o filter) | - |
| Polyolefin IV bag (100 mL) | 0.1 | 0 | 5 | - | - |
| | | 24 | 5 | - | - |
| | | 24 | 25 | - | - |
| | | 24 | 25 | PU (w/o filter) | 27 |
| | | 24 | 25 | PU (with filter) | 27 |
| Syringe (20 mL) | 0.1 | 0 | 5 | - | - |
| | | 24 | 5 | - | - |
| | | 24 | 25 | - | - |
| | | 24 | 25 | PE (w/o filter) | 4 |
| EVA IV bag (100 mL) | 62.5 | 0 | 5 | - | - |
| | | 24 | 5 | - | - |
| | | 24 | 25 | - | - |
| | | 24 | 25 | PVC (w/o filter) | 27 |
| | | 24 | 25 | PE (w/o filter) | - |
| Polyolefin IV bag (100 mL) | 62.5 | 0 | 5 | - | - |
| | | 24 | 5 | - | - |
| | | 24 | 25 | - | - |
| | | 24 | 25 | PU (w/o filter) | 27 |
| | | 24 | 25 | PU (with filter) | 27 |

Fig. 19

| Sample | Result |
|---|---|
| EVA IV bag 0.1 µg/mL T0 #1 | No particles |
| EVA IV bag 0.1 µg/mL 24h 5°C | No particles |
| EVA IV bag 0.1 µg/mL T0 #2 | No particles |
| EVA IV bag 0.1 µg/mL 24h 25°C | No particles |
| EVA IV bag 0.1 µg/mL 24h 25°C PVC (w/o filter) | No particles |
| EVA IV bag 0.1 µg/mL T0 #3 | No particles |
| EVA IV bag 0.1 µg/mL 24h 25°C PE (w/o filter) | No particles |
| EVA IV bag 62.5 µg/mL T0 #1 | No particles |
| EVA IV bag 62.5 µg/mL 24h 5°C | No particles |
| EVA IV bag 62.5 µg/mL T0 #2 | No particles |
| EVA IV bag 62.5 µg/mL 24h 25°C | No particles |
| EVA IV bag 62.5 µg/mL 24h 25°C PVC (w/o filter) | No particles |
| EVA IV bag 62.5 µg/mL T0 #3 | No particles |
| EVA IV bag 62.5 µg/mL 24h 25°C PE (w/o filter) | No particles |
| Polyolefin IV bag 0.1 µg/mL T0 #1 | No particles |
| Polyolefin IV bag 0.1 µg/mL 24h 5°C | No particles |
| Polyolefin IV bag 0.1 µg/mL T0 #2 | No particles |
| Polyolefin IV bag 0.1 µg/mL 24h 25°C | No particles |
| Polyolefin IV bag 0.1 µg/mL 24h 25°C PU (w/o filter) | No particles |
| Polyolefin IV bag 0.1 µg/mL T0 #3 | No particles |
| Polyolefin IV bag 0.1 µg/mL 24h 25°C PU (with filter) | No particles |
| Polyolefin IV bag 62.5 µg/mL T0 #1 | No particles |
| Polyolefin IV bag 62.5 µg/mL 24h 5°C | No particles |
| Polyolefin IV bag 62.5 µg/mL T0 #2 | No particles |
| Polyolefin IV bag 62.5 µg/mL 24h 25°C | No particles |
| Polyolefin IV bag 62.5 µg/mL 24h 25°C PU (w/o filter) | No particles |
| Polyolefin IV bag 62.5 µg/mL T0 #3 | No particles |
| Polyolefin IV bag 62.5 µg/mL 24h 25°C PU (with filter) | No particles |
| Syringe 0.1 µg/mL T0 #1 | No particles |
| Syringe 0.1 µg/mL 24h 5°C | No particles |
| Syringe 0.1 µg/mL T0 #2 | No particles |
| Syringe 0.1 µg/mL 24h 25°C | No particles |
| Syringe 0.1 µg/mL T0 #3 | No particles |
| Syringe 0.1 µg/mL 24h 25°C PE (w/o filter) | No particles |

Fig. 20

| Sample | Average Cumulative Counts Per Container | |
|---|---|---|
| | ≥ 10 µm | ≥ 25 µm |
| EVA IV bag 0.1 µg/mL T0 #1 | 2000 | 0 |
| EVA IV bag 0.1 µg/mL 24h 5°C | 333 | 0 |
| EVA IV bag 0.1 µg/mL T0 #2 | 667 | 0 |
| EVA IV bag 0.1 µg/mL 24h 25°C | 133 | 0 |
| EVA IV bag 0.1 µg/mL 24h 25°C PVC (w/o filter) | 667 | 0 |
| EVA IV bag 0.1 µg/mL T0 #3 | 2800 | 67 |
| EVA IV bag 0.1 µg/mL 24h 25°C PE (w/o filter) | 400 | 0 |
| EVA IV bag 62.5 µg/mL T0 #1 | 1933 | 67 |
| EVA IV bag 62.5 µg/mL 24h 5°C | 267 | 0 |
| EVA IV bag 62.5 µg/mL T0 #2 | 3400 | 0 |
| EVA IV bag 62.5 µg/mL 24h 25°C | 1600 | 0 |
| EVA IV bag 62.5 µg/mL 24h 25°C PVC (w/o filter) | 133 | 0 |
| EVA IV bag 62.5 µg/mL T0 #3 | 1000 | 0 |
| EVA IV bag 62.5 µg/mL 24h 25°C PE (w/o filter) | 333 | 0 |
| Polyolefin IV bag 0.1 µg/mL T0 #1 | 3067 | 0 |
| Polyolefin IV bag 0.1 µg/mL 24h 5°C | 800 | 0 |
| Polyolefin IV bag 0.1 µg/mL T0 #2 | 1867 | 0 |
| Polyolefin IV bag 0.1 µg/mL 24h 25°C | 667 | 0 |
| Polyolefin IV bag 0.1 µg/mL 24h 25°C PU (w/o filter) | 133 | 0 |
| Polyolefin IV bag 0.1 µg/mL T0 #3 | 1800 | 0 |
| Polyolefin IV bag 0.1 µg/mL 24h 25°C PU (with filter) | 0 | 0 |

Fig. 21a

| | | |
|---|---|---|
| Polyolefin IV bag 62.5 µg/mL T0 #1 | 933 | 0 |
| Polyolefin IV bag 62.5 µg/mL 24h 5°C | 2200 | 0 |
| Polyolefin IV bag 62.5 µg/mL T0 #2 | 600 | 0 |
| Polyolefin IV bag 62.5 µg/mL 24h 25°C | 1400 | 0 |
| Polyolefin IV bag 62.5 µg/mL 24h 25°C PU (w/o filter) | 0 | 0 |
| Polyolefin IV bag 62.5 µg/mL T0 #3 | 2267 | 67 |
| Polyolefin IV bag 62.5 µg/mL 24h 25°C PU (with filter) | 267 | 0 |
| Syringe 0.1 µg/mL T0 #1 | 467 | 133 |
| Syringe 0.1 µg/mL 24h 5°C | 267 | 0 |
| Syringe 0.1 µg/mL T0 #2 | 67 | 0 |
| Syringe 0.1 µg/mL 24h 25°C | 333 | 0 |
| Syringe 0.1 µg/mL T0 #3 | 200 | 0 |
| Syringe 0.1 µg/mL 24h 25°C PE (w/o filter) | 267 | 0 |

Fig. 21b

| Sample | % HMW |
|---|---|
| EVA IV bag 62.5 µg/mL T0 #1 | 0.2 |
| EVA IV bag 62.5 µg/mL 24h 5°C | 0.2 |
| EVA IV bag 62.5 µg/mL T0 #2 | 0.2 |
| EVA IV bag 62.5 µg/mL 24h 25°C | 0.2 |
| EVA IV bag 62.5 µg/mL 24h 25°C PVC (w/o filter) | 0.2 |
| EVA IV bag 62.5 µg/mL T0 #3 | 0.2 |
| EVA IV bag 62.5 µg/mL 24h 25°C PE (w/o filter) | 0.2 |
| Polyolefin IV bag 62.5 µg/mL T0 #1 | 0.2 |
| Polyolefin IV bag 62.5 µg/mL 24h 5°C | 0.2 |
| Polyolefin IV bag 62.5 µg/mL T0 #2 | 0.2 |
| Polyolefin IV bag 62.5 µg/mL 24h 25°C | 0.2 |
| Polyolefin IV bag 62.5 µg/mL 24h 25°C PU (w/o filter) | 0.8 |
| Polyolefin IV bag 62.5 µg/mL T0 #3 | 0.2 |
| Polyolefin IV bag 62.5 µg/mL 24h 25°C PU (with filter) | 0.9 |

Fig. 22

| Sample | Protein (µg/mL) | Change* (%) |
|---|---|---|
| EVA IV bag 62.5 µg/mL T0 #1 | 53.2 | |
| EVA IV bag 62.5 µg/mL 24h 5°C | 53.4 | 0.4 |
| EVA IV bag 62.5 µg/mL T0 #2 | 55.2 | |
| EVA IV bag 62.5 µg/mL 24h 25°C | 55.0 | -0.4 |
| EVA IV bag 62.5 µg/mL 24h 25°C PVC (w/o filter) | 52.2 | -5.4 |
| EVA IV bag 62.5 µg/mL T0 #3 | 59.1 | |
| EVA IV bag 62.5 µg/mL 24h 25°C PE (w/o filter) | 58.7 | -0.7 |
| Polyolefin IV bag 62.5 µg/mL T0 #1 | 56.5 | |
| Polyolefin IV bag 62.5 µg/mL 24h 5°C | 54.8 | -3.0 |
| Polyolefin IV bag 62.5 µg/mL T0 #2 | 55.6 | |
| Polyolefin IV bag 62.5 µg/mL 24h 25°C | 55.3 | -0.6 |
| Polyolefin IV bag 62.5 µg/mL 24h 25°C PU (w/o filter) | 55.6 | 0.0 |
| Polyolefin IV bag 62.5 µg/mL T0 #3 | 54.7 | |
| Polyolefin IV bag 62.5 µg/mL 24h 25°C PU (with filter) | 54.4 | -0.5 |

Fig. 23

| Sample | Protein (μg/mL) | Change* (%) |
|---|---|---|
| EVA IV bag 0.1 μg/mL T0 #1 | 0.111 | |
| EVA IV bag 0.1 μg/mL 24h 5°C | 0.110 | -0.9 |
| EVA IV bag 0.1 μg/mL T0 #2 | 0.111 | |
| EVA IV bag 0.1 μg/mL 24h 25°C | 0.107 | -3.6 |
| EVA IV bag 0.1 μg/mL 24h 25°C PVC (w/o filter) | 0.105 | -5.4 |
| EVA IV bag 0.1 μg/mL T0 #3 | 0.110 | |
| EVA IV bag 0.1 μg/mL 24h 25°C PE (w/o filter) | 0.110 | 0.0 |
| EVA IV bag 62.5 μg/mL T0 #1 | 68.0 | |
| EVA IV bag 62.5 μg/mL 24h 5°C | 64.2 | -5.6 |
| EVA IV bag 62.5 μg/mL T0 #2 | 66.6 | |
| EVA IV bag 62.5 μg/mL 24h 25°C | 69.0 | 3.6 |
| EVA IV bag 62.5 μg/mL 24h 25°C PVC (w/o filter) | 68.3 | 2.6 |
| EVA IV bag 62.5 μg/mL T0 #3 | 73.5 | |
| EVA IV bag 62.5 μg/mL 24h 25°C PE (w/o filter) | 71.3 | -3.0 |
| Polyolefin IV bag 0.1 μg/mL T0 #1 | 0.105 | |
| Polyolefin IV bag 0.1 μg/mL 24h 5°C | 0.105 | 0.0 |
| Polyolefin IV bag 0.1 μg/mL T0 #2 | 0.101 | |
| Polyolefin IV bag 0.1 μg/mL 24h 25°C | 0.099 | -2.0 |
| Polyolefin IV bag 0.1 μg/mL 24h 25°C PU (w/o filter) | 0.102 | 1.0 |
| Polyolefin IV bag 0.1 μg/mL T0 #3 | 0.102 | |
| Polyolefin IV bag 0.1 μg/mL 24h 25°C PU (with filter) | 0.101 | 1.0 |
| Polyolefin IV bag 62.5 μg/mL T0 #1 | 68.5 | |
| Polyolefin IV bag 62.5 μg/mL 24h 5°C | 69.7 | 1.8 |
| Polyolefin IV bag 62.5 μg/mL T0 #2 | 69.1 | |
| Polyolefin IV bag 62.5 μg/mL 24h 25°C | 67.4 | -2.5 |
| Polyolefin IV bag 62.5 μg/mL 24h 25°C PU (w/o filter) | 68.0 | -1.6 |
| Polyolefin IV bag 62.5 μg/mL T0 #3 | 70.3 | |
| Polyolefin IV bag 62.5 μg/mL 24h 25°C PU (with filter) | 66.5 | -5.4 |
| Syringe 0.1 μg/mL T0 #1 | 0.106 | |
| Syringe 0.1 μg/mL 24h 5°C | 0.104 | -1.9 |
| Syringe 0.1 μg/mL T0 #2 | 0.107 | |
| Syringe 0.1 μg/mL 24h 25°C | 0.102 | -4.7 |
| Syringe 0.1 μg/mL T0 #3 | 0.108 | |
| Syringe 0.1 μg/mL 24h 25°C PE (w/o filter) | 0.104 | -3.7 |

Fig. 24

| Sample | Relative Potency (%) |
|---|---|
| EVA IV bag 62.5 µg/mL T0 #1 | 73 |
| EVA IV bag 62.5 µg/mL 24h 5°C | 71 |
| EVA IV bag 62.5 µg/mL T0 #2 | 77 |
| EVA IV bag 62.5 µg/mL 24h 25°C | 75 |
| EVA IV bag 62.5 µg/mL 24h 25°C PVC (w/o filter) | 76 |
| EVA IV bag 62.5 µg/mL T0 #3 | 79 |
| EVA IV bag 62.5 µg/mL 24h 25°C PE (w/o filter) | 81 |
| Polyolefin IV bag 62.5 µg/mL T0 #1 | 79 |
| Polyolefin IV bag 62.5 µg/mL 24h 5°C | 81 |
| Polyolefin IV bag 62.5 µg/mL T0 #2 | 80 |
| Polyolefin IV bag 62.5 µg/mL 24h 25°C | 78 |
| Polyolefin IV bag 62.5 µg/mL 24h 25°C PU (w/o filter) | 79 |
| Polyolefin IV bag 62.5 µg/mL T0 #3 | 74 |
| Polyolefin IV bag 62.5 µg/mL 24h 25°C PU (with filter) | 75 |

Fig. 25

| IV Bag Material | AMG 562 Concentration in Solution | % IVSS | Storage (hours) | Temperature (°C) |
|---|---|---|---|---|
| Siliconized disposable syringe | 50 ng/mL | 5 | 24 | 25°C |
| Siliconized disposable syringe | 10 µg/mL | 5 | 24 | 25°C |
| Ethyl vinyl acetate | 50 ng/mL | 5 | 24 | 25°C |
| Ethyl vinyl acetate | 10 µg/mL | 5 | 24 | 25°C |
| Ethyl vinyl acetate* | 50 ng/mL | 0 | 24 | 25°C |
| Polyolefin | 50 ng/mL | 5 | 24 | 25°C |
| Polyolefin | 10 µg/mL | 5 | 24 | 25°C |
| *Polyolefin | 50 ng/mL | 0 | 24 | 25°C |

Fig. 26

| IV Bag Material | AMG 562 Concentration in Solution | % IVSS | % Recovery after 24 hours at 25°C |
|---|---|---|---|
| Siliconized disposable syringe | 50 ng/ml | 5 | 104 |
| Siliconized disposable syringe | 10 µg/mL | 5 | 103 |
| Ethyl vinyl acetate | 50 ng/mL | 5 | 109 |
| Ethyl vinyl acetate | 10 µg/mL | 5 | 107 |
| Ethyl vinyl acetate | 50 ng/mL | 0 | 47 |
| Polyolefin | 50 ng/mL | 5 | 106 |
| Polyolefin | 10 µg/mL | 5 | 105 |
| Polyolefin | 50 ng/mL | 0 | 31 |

Fig. 27

| IV bag material and AMG 562 concentration | % IVSS | % HMW | |
|---|---|---|---|
| | | T=0 | T=24 hours at 25°C |
| Siliconized disposable syringe 10 µg/mL | 5 | 0.4% | 0.4% |
| Ethyl vinyl acetate 10 µg/mL | 5 | 0.4% | 0.4% |
| Polyolefin 10 µg/mL | 5 | 0.4% | 0.4% |

Fig. 28

| IV bag material and AMG 562 concentration | % IVSS | ≥10 µm Average Cumulative Particle Counts/mL | |
|---|---|---|---|
| | | T=0 | T=24 hours at 25°C |
| Siliconized disposable syringe 50 ng/mL | 5 | 8 | 1 |
| Siliconized disposable syringe 10 µg/mL | 5 | 18 | 2 |
| Ethyl vinyl acetate 50 ng/mL | 5 | 9 | 6 |
| Ethyl vinyl acetate 10 µg/mL | 5 | 18 | 3 |
| Polyolefin 50 ng/ml | 5 | 9 | 8 |
| Polyolefin10 µg/mL | 5 | 12 | 5 |
| IV bag material and AMG 562 concentration | % IVSS | ≥25 µm Average Cumulative Particle Counts/mL | |
| | | T=0 | T=24 hours at 25°C |
| Siliconized disposable syringe 50 ng/mL | 5 | 0 | 0 |
| Siliconized disposable syringe 10 µg/mL | 5 | 1 | 0 |
| Ethyl vinyl acetate 50 ng/mL | 5 | 1 | 0 |
| Ethyl vinyl acetate 10 µg/mL | 5 | 0 | 0 |
| Polyolefin 50 ng/ml | 5 | 1 | 1 |
| Polyolefin10 µg/mL | 5 | 2 | 0 |

Fig. 29

| IV bag material and AMG 562 concentration | % IVSS | Relative potency (%) | |
|---|---|---|---|
| | | T=0 | T=24 hours at 25°C |
| Siliconized disposable syringe 10 µg/mL | 5 | 93 ± 5 | 83 ± 11 |
| Ethyl vinyl acetate 10 µg/mL | 5 | 93 ± 5 | 87 ± 14 |
| Polyolefin 10 µg/mL | 5 | 97 ± 5 | 91 ± 10 |

Fig. 30

| IV Material Type | Concentration of AMG 757 | Temperature | Time |
|---|---|---|---|
| Ethyl vinyl acetate (IV bag) | 2 µg/mL | 2°C to 8°C | 0, 4 h and 24 h[a] |
| | | 25°C | 0, 4 h and 24 h[a] |
| | 1 mg/mL | 2°C to 8°C | 0, 4 h and 24 h[a] |
| | | 25°C | 0, 4 h and 24 h[a] |
| Polyolefin (IV bag) | 2 µg/mL | 2°C to 8°C | 0, 4 h and 24 h[a] |
| | | 25°C | 0, 4 h and 24 h[a] |
| | 1 mg/mL | 2°C to 8°C | 0, 4 h and 24 h[a] |
| | | 25°C | 0, 4 h and 24 h[a] |
| Syringe (60 cc) | 2 µg/mL | 2°C to 8°C | 0, 4 h and 24 h[a] |
| | | 25°C | 0, 4 h and 24 h[a] |

Fig. 31

| Container | t = 0 | t = 0 | t = 24 h[a] |
|---|---|---|---|
| 2 µg/mL AMG 757 EVA 2°C to 8°C | No Particles | No Particles | No Particles |
| 2 µg/mL AMG 757 EVA 25°C | No Particles | No Particles | No Particles |
| 2 µg/mL AMG 757 Polyolefin 2°C to 8°C | No Particles | No Particles | No Particles |
| 2 µg/mL AMG 757 Polyolefin 25°C | No Particles | No Particles | No Particles |
| 2 µg/mL AMG 757 Syringe 2°C to 8°C | No Particles | No Particles | No Particles |
| 2 µg/mL AMG 757 Syringe 25°C | No Particles | No Particles | No Particles |
| 1 mg/mL AMG 757 EVA 2°C to 8°C | No Particles | No Particles | No Particles |
| 1 mg/mL AMG 757 EVA 25°C | No Particles | No Particles | No Particles |
| 1 mg/mL AMG 757 Polyolefin 2°C to 0°C | No Particles | No Particles | No Particles |
| 1 mg/mL AMG 757 Polyolefin 25°C | No Particles | No Particles | No Particles |

Fig. 32

| | Average Cumulative Counts/Container | | |
|---|---|---|---|
| 10 micron | t = 0 | t = 4 h | t = 24 h[a] |
| 2 µg/mL EVA 2°C to 8°C | 0 | 0 | 0 |
| 2 µg/mL EVA 25°C | 166 | 166 | 0 |
| 2 µg/mL Polyolefin 2°C to 8°C | 666 | 0 | 0 |
| 2 µg/mL Polyolefin 25°C | 500 | 0 | 0 |
| 2 µg/mL Syringe 2°C to 8°C | 0 | 0 | 0 |
| 2 µg/mL Syringe 25°C | 100 | 0 | 0 |
| 1 mg/mL EVA 2°C to 8°C | 2300 | 333 | 0 |
| 1 mg/mL EVA 25°C | 666 | 500 | 0 |
| 1 mg/mL Polyolefin 2°C to 0°C | 500 | 500 | 0 |
| 1 mg/mL Polyolefin 25°C | 1000 | 333 | 0 |
| 25 micron | t = 0 | t = 4 h | t = 24 h[a] |
| 2 µg/mL EVA 2°C to 8°C | 0 | 0 | 0 |
| 2 µg/mL EVA 25°C | 0 | 0 | 0 |
| 2 µg/mL Polyolefin 2°C to 8°C | 0 | 0 | 0 |
| 2 µg/mL Polyolefin 25°C | 0 | 0 | 0 |
| 2 µg/mL Syringe 2°C to 8°C | 0 | 0 | 0 |
| 2 µg/mL Syringe 25°C | 0 | 0 | 0 |
| 1 mg/mL EVA 2°C to 8°C | 166 | 0 | 0 |
| 1 mg/mL EVA 25°C | 166 | 0 | 0 |
| 1 mg/mL Polyolefin 2°C to 0°C | 0 | 0 | 0 |
| 1 mg/mL Polyolefin 25°C | 0 | 0 | 0 |

Fig. 33

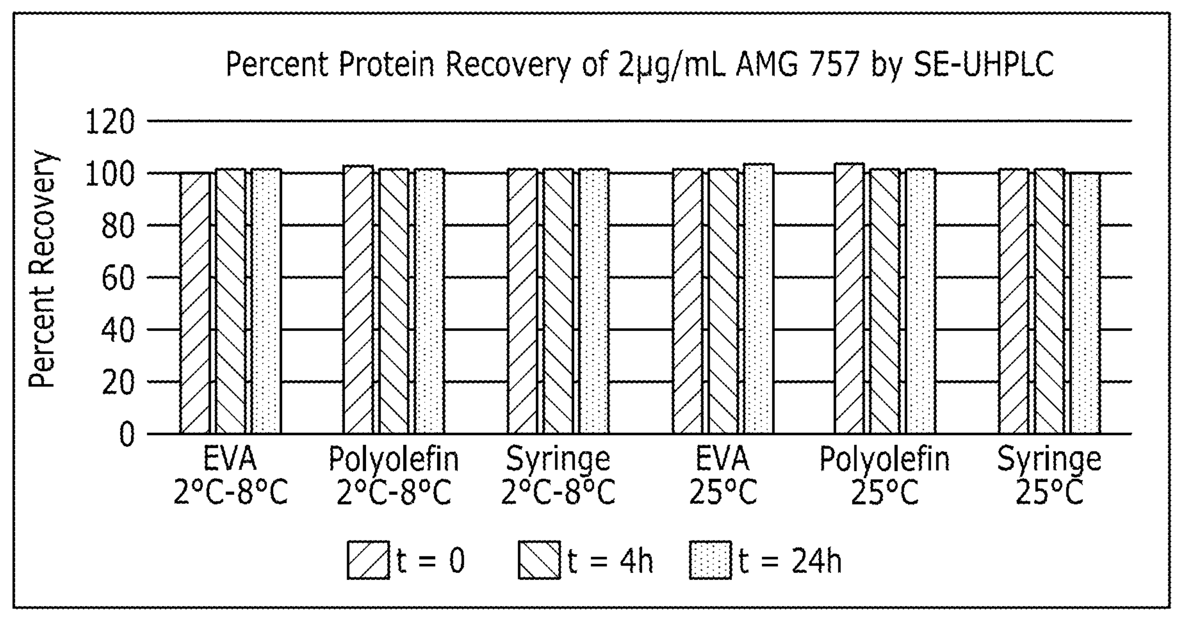
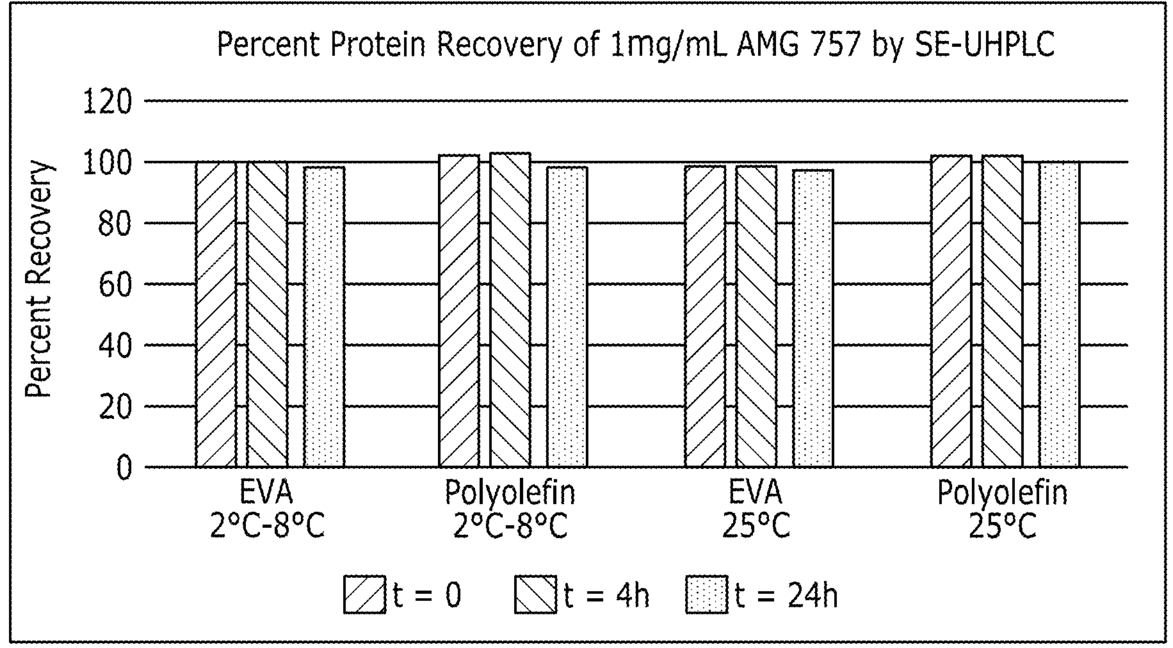
Fig. 34

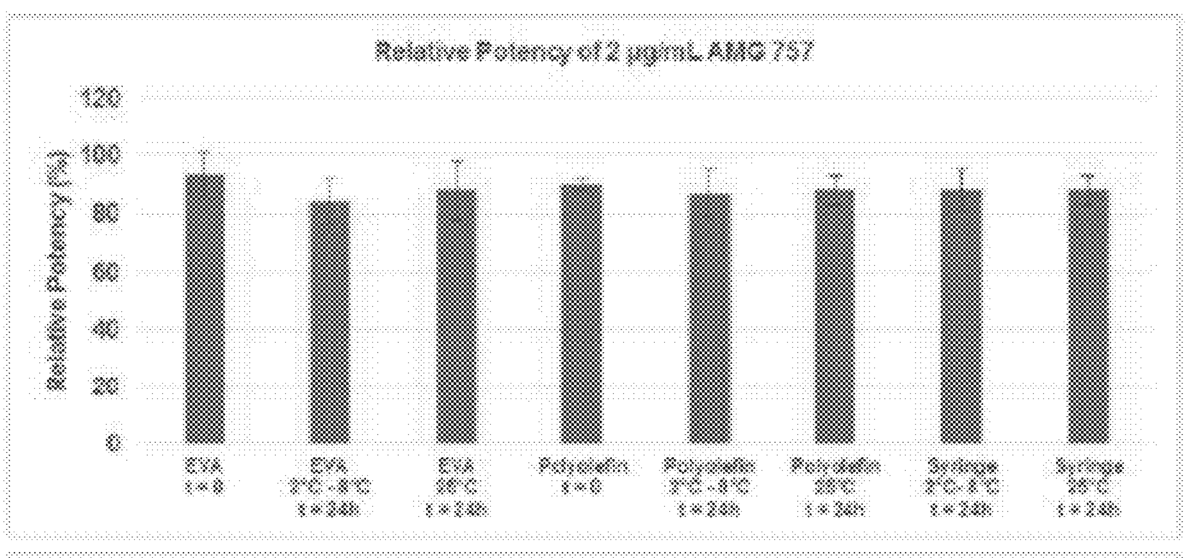
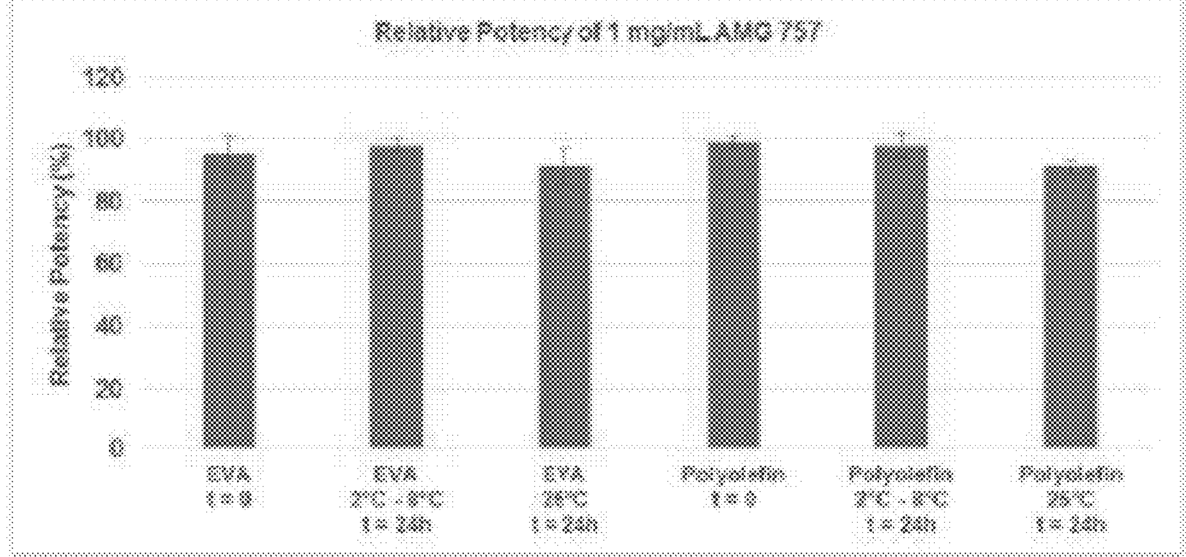
Fig. 35

SEQUENCE LISTING

<160> NUMBER OF SEQ ID NOS: 3

<210> SEQ ID NO 1
<211> LENGTH: 485
<212> TYPE: PRT
<213> ORGANISM: Artificial Sequence
<220> FEATURE:
<223> OTHER INFORMATION: Synthetic Polypeptide

<400> SEQUENCE: 1

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ile Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Ala Asn Ile Thr Met Thr Tyr Tyr Ala Asp
50 55 60

Ser Val Lys Gly Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asp Ser Tyr Val Ser Trp Phe
100 105 110

Ala Tyr Trp Gly Gln Gly Thr Leu Val Thr Val Ser Ser Gly Lys Pro
115 120 125

Gly Ser Gly Lys Pro Gly Ser Gly Lys Pro Gly Ser Gly Glu Pro Gly
130 135 140

Ser Gln Ala Val Val Thr Gln Glu Pro Ser Leu Thr Val Ser Pro Gly
145 150 155 160

Gly Thr Val Thr Leu Thr Cys Gly Ser Ser Thr Gly Ala Val Thr Thr
165 170 175

Ser Asn Tyr Ala Asn Trp Val Gln Gln Lys Pro Gly Lys Ser Pro Arg
180 185 190

Gly Leu Ile Gly Gly Thr Asn Lys Arg Ala Pro Gly Val Pro Ala Arg
195 200 205

Phe Ser Gly Ser Leu Leu Gly Gly Lys Ala Ala Leu Thr Ile Ser Gly
210 215 220

Ala Gln Pro Glu Asp Glu Ala Asp Tyr Tyr Cys Ala Leu Trp Tyr Ser
225 230 235 240

```
Asn His Trp Val Phe Gly Gly Gly Thr Lys Leu Thr Val Leu Glu Pro
                245                 250                 255

Lys Ser Ser Asp Lys Thr His Thr Cys Pro Pro Cys Pro Ala Pro Pro
            260                 265                 270

Val Ala Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Lys His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Glu Ala Leu Pro Ala
        355                 360                 365

Pro Ile Glu Lys Thr Ile Ser Glu Ala Glu Gly Gln Pro Arg Glu Pro
    370                 375                 380

Gln Val Tyr Thr Leu Pro Pro Ser Arg Glu Cys Met Thr Lys Asn Gln
385                 390                 395                 400

Val Lys Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Ile Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Lys
                485


<210> SEQ ID NO 2
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Ser
            20                  25                  30

Trp Asn Met Trp Val Arg Gln Ala Pro Gly Lys Gly Leu Glu Trp Val
        35                  40                  45

Ser Glu Ile Asn Pro Asp Ser Ser Thr Ile Asn Tyr Ala Thr Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Asn Trp Phe Pro Tyr Trp Gly Gln Gly Thr Leu Val
            100                 105                 110
```

```
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Ile Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asp Thr
        195                 200                 205

Lys Val Asp Lys Lys Val Glu Pro Lys Ser Cys Asp Lys Thr His Thr
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Lys His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Glu Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Asp Val Ser
        355                 360                 365

Gly Phe Tyr Pro Ser Asp Ile Ala Val Glu Trp Glu Ser Asp Gly Gln
    370                 375                 380

Pro Glu Asn Asn Tyr Lys Thr Ile Pro Pro Val Leu Asp Ser Asp Gly
385                 390                 395                 400

Ser Phe Phe Leu Tyr Ser Lys Leu Thr Val Asp Lys Ser Arg Trp Glu
                405                 410                 415

Gln Gly Asp Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 3
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 3

```
Asp Ile Val Met Thr Gln Ser Pro Ser Ser Leu Ser Ala Ser Val Gly
1               5                   10                  15

Asp Arg Val Ile Ile Thr Cys Arg Ala Ser Gln Asn Val Asp Thr Trp
            20                  25                  30
```

-continued

```
Val Ala Asn Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Thr Ile Phe Cys Gln Gln Tyr Asp Ser Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Glu Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

SYSTEMS AND APPROACHES FOR DRUG DELIVERY

CROSS-REFERENCE TO RELATED APPLICATION

This is the United States national phase of International Patent Application No. PCT/US20/57054, filed Oct. 23, 2020, which claims priority to U.S. Application No. 62/925,685, filed Oct. 24, 2019, the entire contents of each of which being incorporated by reference herein.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "50058_Seqlisting.txt", which was created on Aug. 8, 2022 and is 10,362 bytes in size. The subject matter of the Sequence Listing is incorporated herein in its entirety by reference.

FIELD OF DISCLOSURE

The present disclosure generally relates to drug delivery systems and, more particularly, to material compatibility and component compatibility for drug therapies, drug delivery devices, and/or drug delivery systems.

BACKGROUND

Drugs are administered to treat a variety of conditions and diseases. Intravenous ("IV") therapy is a drug dosing process that delivers drugs directly into a patient's vein using an infusion contained in a delivery container (e.g., a pliable bag). These drug dosings may be performed in a healthcare facility, or in some instances, at remote locations such as a patient's home. In certain applications, a drug product may be shipped to a healthcare facility (e.g., an inpatient facility, an outpatient facility, and/or a pharmacy) in a powdered or lyophilized form.

When reconstituting these drugs for administration, it is of particular importance to maintain a sterile environment so as to not taint or otherwise damage the quality of the drug. Additionally, some classes of drugs such as bi-specific T-cell engagers may require exceptionally accurate quantities of the drug product and/or other fluids required for dosing so as to prevent the drug product from becoming toxic. Oftentimes, the healthcare professional must prepare the drug by closely following a set of steps to ensure a sterile environment is maintained and that correct quantities of ingredients are added to the delivery container. When reconstituting these drugs for administration, it may be desirable or necessary to utilize a diluent, such as by adding a diluent to a drug product vial. As a result of these various steps and requirements, the reconstitution process may be time-consuming, tedious, and may have an unacceptable or undesirable error rate.

The current process of reconstituting a lyophilized oncology product is often performed either at the hospital or the specialty compounding pharmacy by a licensed pharmacist. The use of a hood is often required to perform reconstitution steps to provide a sterile working environment which can be cumbersome for pharmacists given the complexity of the steps. In addition, this admixing process involves the use of multiple needles to withdraw/add sterile water for injection (WFI), saline and/or Intravenous Solution Stabilizer (IVSS) solutions. Typically, for relatively complex oncology products such as a Bi-specific T-cell Engager (BiTE®) molecule (e.g. Blincyto®) prepared in an IV bag, a specified volume of WFI is added to reconstitute a lyophilized drug product contained in a vial via the use of a needle and syringe system. Next, the applicable volume of saline and IVSS solutions are added to an empty IV bag before the final reconstituted drug product is introduced.

It may also be of particular importance to utilize materials for device and system components that are compatible with the drug therapy components, for example materials that do not degrade, deactivate, contaminate, or otherwise negatively affect the drug therapy components. It may be desirable to assess the compatibility of each or a group of molecules in major classes of plastic chemistries that are being used worldwide; however testing them all is resource intensive and unsustainable as the materials are ever changing. Few techniques allow one to determine and eventually tune the compatibility and optimize the IVSS for all of a group of molecules.

In addition, with the current regulatory requirements implemented by National Institute for Occupational Safety and Health (NIOSH), certain oncology products are included in the hazardous drug list which require the use of additional engineering controls such as Closed System Transfer Device (CSTD) as an additional means of protection. Also, regardless of whether a drug is on the NIOSH list, it may be advantageous to utilize a CSTD and/or other components/systems to minimize or avoid undesired release of fumes into the air or other exposures.

As described in more detail below, the present disclosure sets forth systems and methods for drug delivery device reconstitution embodying advantageous alternatives to existing systems and methods, and that may address one or more of the challenges or needs mentioned herein, as well as provide other benefits and advantages.

SUMMARY

In accordance with a first aspect, an approach for determining material compatibility for components of a drug delivery system is provided that includes using a surface zeta-potential analytical method to evaluate surface interactions between a desired molecule and at least one material present within a given IV-bag system. In some examples, the approach includes the steps of providing a double gap flow cell having a top layer, a bottom layer, and a flow path for the desired molecule to flow there between, and measuring a first zeta-potential when the desired molecule flows through the first potential material. The top and bottom layers are constructed from a first potential material.

In some examples, the approach further includes the steps of replacing the first potential material with a second potential material. Further, a second zeta-potential of the desired molecule is measured while flowing through the second potential material. The first zeta-potential is compared with the second zeta-potential.

In some of these examples, the desired molecule includes a drug product to be delivered intravenously. In some examples, a solution is formed with the drug product and an intravenous solution stabilizer. The zeta-potential of the solution may then be measured.

In accordance with a second aspect, a drug delivery system for delivering a medicament includes a drug container, a fluid path that receives the drug product from the drug product container, and a drug delivery device positioned along and/or adjacent to the fluid path. The drug container contains a B-cell maturation antigen Bispecific T-Cell engager (BiTE®). The drug delivery device includes a housing, a fluid displacement assembly at least partially supported by and/or surrounded by the housing, and a drive component at least partially supported by and/or surrounded by the housing. The drive component drives the medicament through the fluid displacement assembly. The drug product container is constructed from at least one of ethylvinyl acetate ("EVA") or polyolefin and the fluid path is constructed from at least one of polyethylene, polyurethane, or polyvinyl chloride ("PVC").

In accordance with a third aspect, a drug delivery system for delivering a medicament includes a drug container, a fluid path that receives the drug product from the drug product container, and a drug delivery device positioned along and/or adjacent to the fluid path. The drug container contains a humanized bi-specific XmAb T cell recruiting antibody. The drug delivery device includes a housing, a fluid displacement assembly at least partially supported by and/or surrounded by the housing, and a drive component at least partially supported by and/or surrounded by the housing. The drive component drives the medicament through the fluid displacement assembly. The drug product container and the fluid path are constructed from at least one of EVA or polyolefin.

In accordance with a fourth aspect, a drug delivery system for delivering a medicament includes a drug container, a fluid path that receives the drug product from the drug product container, and a drug delivery device positioned along and/or adjacent to the fluid path. The drug container contains a prostate-specific membrane antigen bispecific T-Cell Engager (BiTE®). In some examples, the BiTE® is a half-life extended (HLE) BiTE®. The drug delivery device includes a housing, a fluid displacement assembly at least partially supported by and/or surrounded by the housing, and a drive component at least partially supported by and/or surrounded by the housing. The drive component drives the medicament through the fluid displacement assembly. The drug product container is constructed from at least one of EVA or polyolefin and the fluid path is constructed from at least one of polyethylene, polyurethane, or PVC.

In accordance with a fifth aspect, a drug delivery system for delivering a medicament includes a drug container, a fluid path that receives the drug product from the drug product container, and a drug delivery device positioned along and/or adjacent to the fluid path. The drug container contains a half-life extended CD19-targeting bispecific T-Cell Engager (BiTE®) antibody. The drug delivery device includes a housing, a fluid displacement assembly at least partially supported by and/or surrounded by the housing, and a drive component at least partially supported by and/or surrounded by the housing. The drive component drives the medicament through the fluid displacement assembly. The drug product container and fluid path are constructed from at least one of EVA or polyolefin.

In accordance with a fifth aspect, a drug delivery system for delivering a medicament includes a drug container, a fluid path that receives the drug product from the drug product container, and a drug delivery device positioned along and/or adjacent to the fluid path. The drug container contains a DLL3-targeting Bispecific T-Cell engager (BiTE®). The drug delivery device includes a housing, a fluid displacement assembly at least partially supported by and/or surrounded by the housing, and a drive component at least partially supported by and/or surrounded by the housing. The drive component drives the medicament through the fluid displacement assembly. The drug product container and fluid path are constructed from at least one of EVA or polyolefin.

BRIEF DESCRIPTION OF THE DRAWINGS

The above needs are at least partially met through provision of the systems and approaches for drug delivery device reconstitution described in the following detailed description, particularly when studied in conjunction with the drawings, wherein:

FIG. 9 is a table illustrating subvisible particle counts measured by light obscuration in accordance with various embodiments;

FIG. 10 is a table illustrating HMW protein species measured by size exclusion chromatography in accordance with various embodiments;

FIGS. 11*a* and 11*b* are tables illustrating SPR binding assay for protein titer in accordance with various embodiments;

FIG. 12 is a table illustrating binding assay for relative potency in accordance with various embodiments;

FIG. 13 is a schematic structure of AMG 424 in accordance with various embodiments;

FIG. 14 is an amino acid sequence of AMG 424 scFv-Fc (SEQ ID NO: 1), heavy chain (SEQ ID NO: 2), and light chain (SEQ ID NO: 3) in accordance with various embodiments;

FIG. 15 is a table illustrating a list of IV administration containers and AMG 424 concentrations in accordance with various embodiments;

FIG. 16 is a table illustrating visual inspection results for AMG 424 in EVA IV bags and polyolefin IV bags in accordance with various embodiments;

FIG. 17 is a table illustrating subvisible particle counts measured by light obscuration in accordance with various embodiments;

FIG. 18 illustrates AMG 424 protein concentration recovery by RP-UHPLC (low dose) and UV-Visible light spectroscopy (high dose) in accordance with various embodiments;

FIG. 19 is a table illustrating a list of IV administration containers and AMG 160 concentrations in accordance with various embodiments;

FIG. 20 is a table illustrating visual inspection results for AMG 160 in EVA and polyolefin IV bags and disposable syringes in accordance with various embodiments;

FIGS. 21a & b are tables illustrating subvisible particle counts measured by light obscuration in accordance with various embodiments;

FIG. 22 is a table illustrating HMW protein species measurements via SE-UHPLC for AMG 160 in accordance with various embodiments;

FIG. 23 is a table illustrating protein concentration measured by SE-UHPLC for AMG 160 in accordance with various embodiments;

FIG. 24 is a table illustrating protein concentration measured by SPR Binding assay for AMG 160 in accordance with various embodiments;

FIG. 25 is a table illustrating binding assay for relative potency for AMG 160 in accordance with various embodiments;

FIG. 26 is a table illustrating a list of IV material types tested and AMG 562 concentrations in accordance with various embodiments;

FIG. 27 is a table illustrating protein recovery by Affinity Protein A HPLC total area counts in accordance with various embodiments;

FIG. 28 in a table illustrating percent HMW species measured by SE-UHPLC accordance with various embodiments;

FIG. 29 is a table illustrating sub-visible particle counts measured by HIAC in accordance with various embodiments;

FIG. 30 is a table illustrating binding assay for relative potency in accordance with various embodiments;

FIG. 31 is a table illustrating a list of IV administration containers and AMG 757 concentrations in accordance with various embodiments;

FIG. 32 is a table illustrating visual inspection results for AMG 757 in accordance with various embodiments;

FIG. 33 is a table illustrating subvisible particle counts measured by light obscuration in accordance with various embodiments in accordance with various embodiments;

FIG. 34 illustrates SE-UHLPC assay for protein recovery in accordance with various embodiments;

FIG. 35 illustrates relative potency of AMG 757 in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Figure 6:
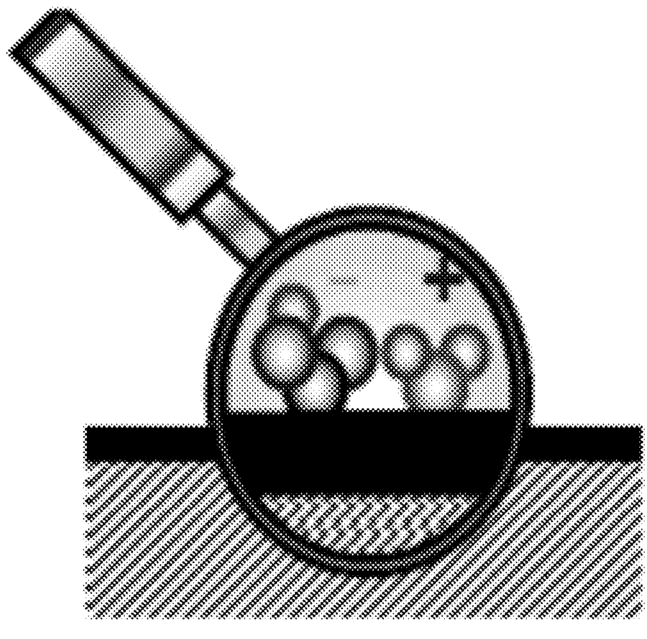
FIG. 6 illustrates a close-up IV container having molecules being adsorbed therein in accordance with various embodiments.

Intravenous solution stabilizer (IVSS) was developed to prevent BiTE® adsorption to surfaces. Few techniques allow us to determine and eventually tune the level of adsorption and optimize the IVSS for our molecules. The surface zeta-potential analytical method was used to understand the surface interactions between a BiTE® and two common IV-bag material types. This technique may support optimization of the IVSS formulation and enable the use of a range of materials in clinics worldwide BiTE® molecules are powerful tools in our cancer fighting arsenal. These unique molecules are very potent and often administered in relatively low concentrations. Unfortunately, BiTE® molecules tend to adhere to surfaces in the low concentration dosing regimes. To prevent BiTE® adsorption to surfaces (an example of such adsorption being depicted in FIG. 6), an intravenous solution stabilizer (IVSS) may be utilized. Additionally, other IV-administration materials and supplies may be used administer these therapies.

Figure 1:
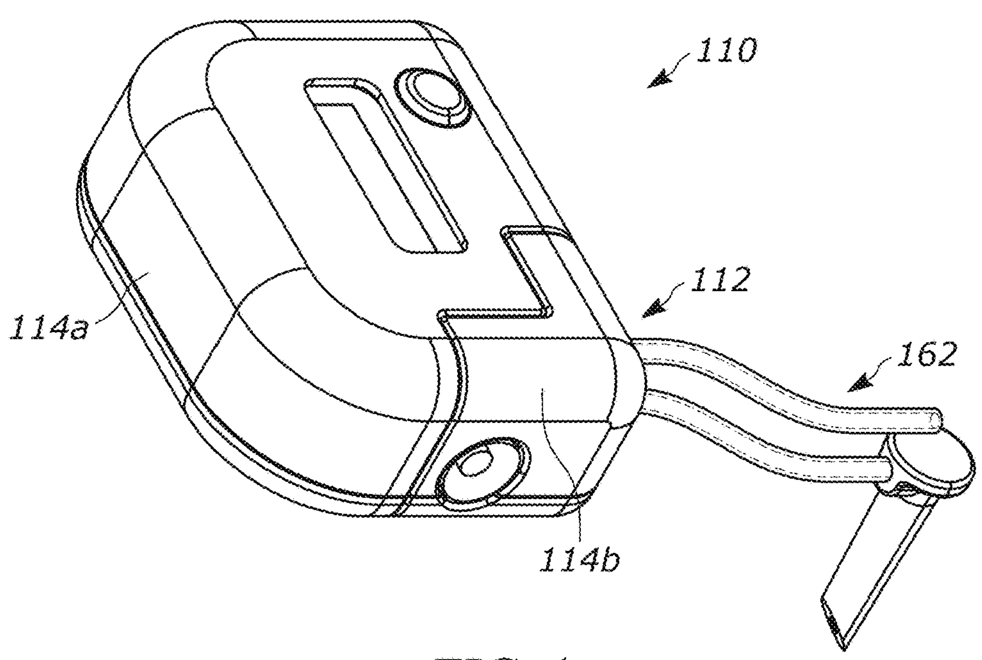
FIG. 1 illustrates an example drug delivery device in accordance with various embodiments.
Figure 2:
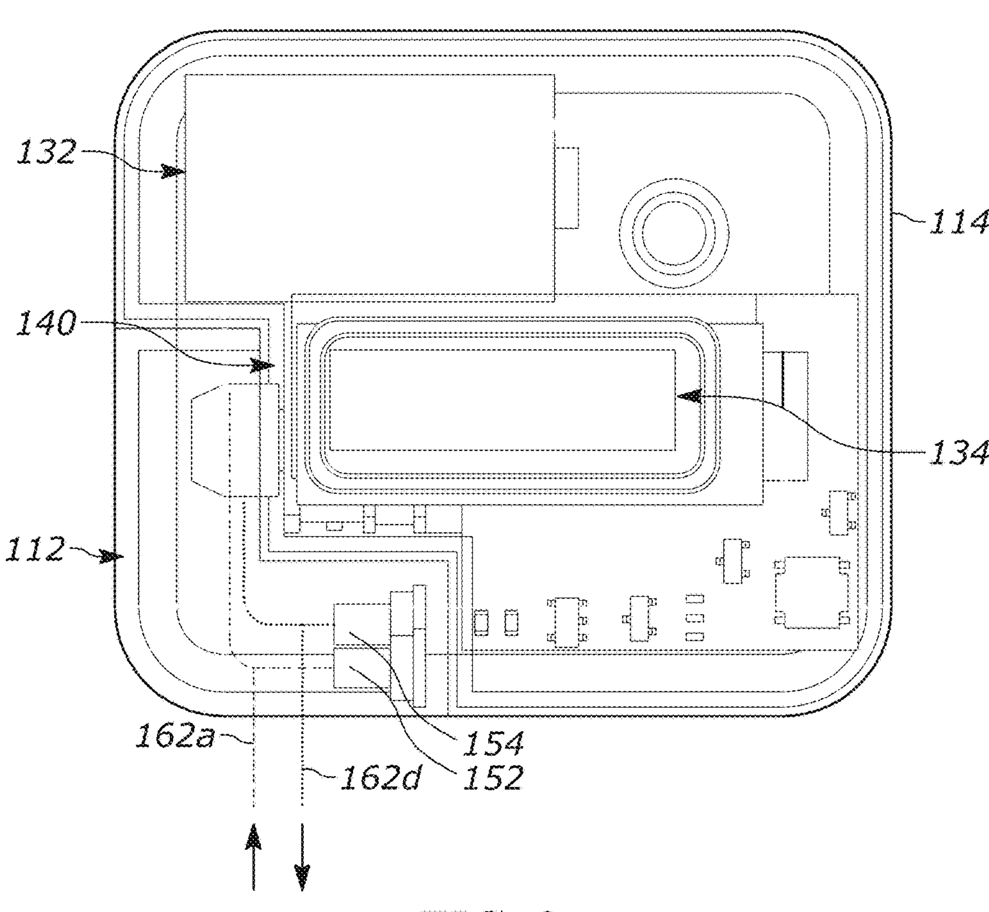
FIG. 2 illustrates a partial cross-section of an example drug delivery device in accordance with various embodiments.

An example drug delivery system and device that may be used to administer a drug product such as BiTE® is illustrated in FIGS. 1-5. More specifically, FIGS. 1 and 2 show a drug delivery device such as a pump 110 having, generally, a pump head 112 having a durable or reusable housing 114a, disposable housing 114b, a fluid flow path 162, a power source such as a battery 132, a drive assembly such as a motor 140, a controller and display 134, and a pair of pressure sensors (e.g., inlet pressure transducer 152 and outlet pressure transducer 154). The two housing components 114a, 114b cooperate to define the overall housing 114. In some examples, the durable or reusable housing 114a may be disposable as suitable. Similarly, in some examples, the disposable housing 114b may be reusable, although certain sterilization and/or refurbishment steps may be required or desirable to achieve this reusability.

As is further illustrated in FIG. 2, a medicament from a drug product container may travel through an input tube, into the pump head 112, and out of the pump through an output tube. In other words, the pump is able to urge the medicament through the pump head 112. While the pump head 112 shown in FIG. 2 is a peristaltic pump but other suitable configurations may be used, such as a positive displacement pump. The pump head 112 shown in FIGS. 1 and 2 is a ring pump that utilizes a generally circular-shaped loop of tubing 162 to create peristaltic forces. As a more specific example, the pump head 112 has a component that pinches or otherwise occludes the ring-shaped tube section in a circular motion to urge fluid through the tube 162.

Figure 3:
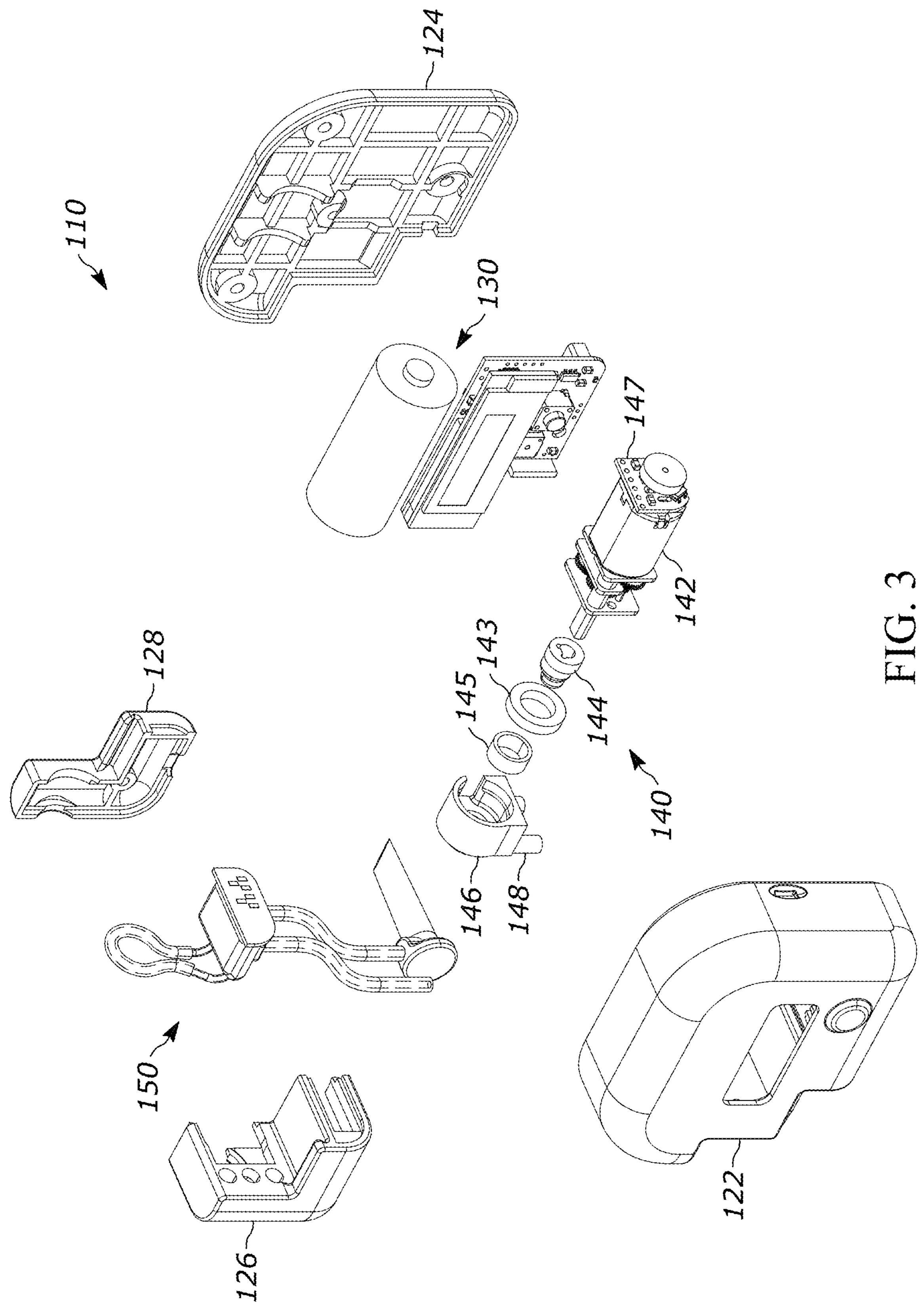
FIG. 3 illustrates an exploded view of an example drug delivery device in accordance with various embodiments.

FIG. 3 shows an exploded view of the pump 110, including sub components of the housing 114, such as a controller front case 122, a controller rear case 124, a pump head front case 126, and a pump head rear case 128. These four components 122, 124, 126, 128 generally fit together to form at least the majority of the housing 114. These four components 122, 124, 126, 128 may be made of a generally rigid and lightweight material, such as plastic, a composite, or any other suitable material. The front/rear paired components (122, 124 on one hand, and 126, 128 on the other) may fit together via fasteners, snap-fit connections, an adhesive, or any other suitable coupling components/methods. A PCA and battery assembly 130 is at least partially contained within the housing 114, with a display screen 134 (FIG. 2) defining a portion of the housing 114.

Figures 4, 5:
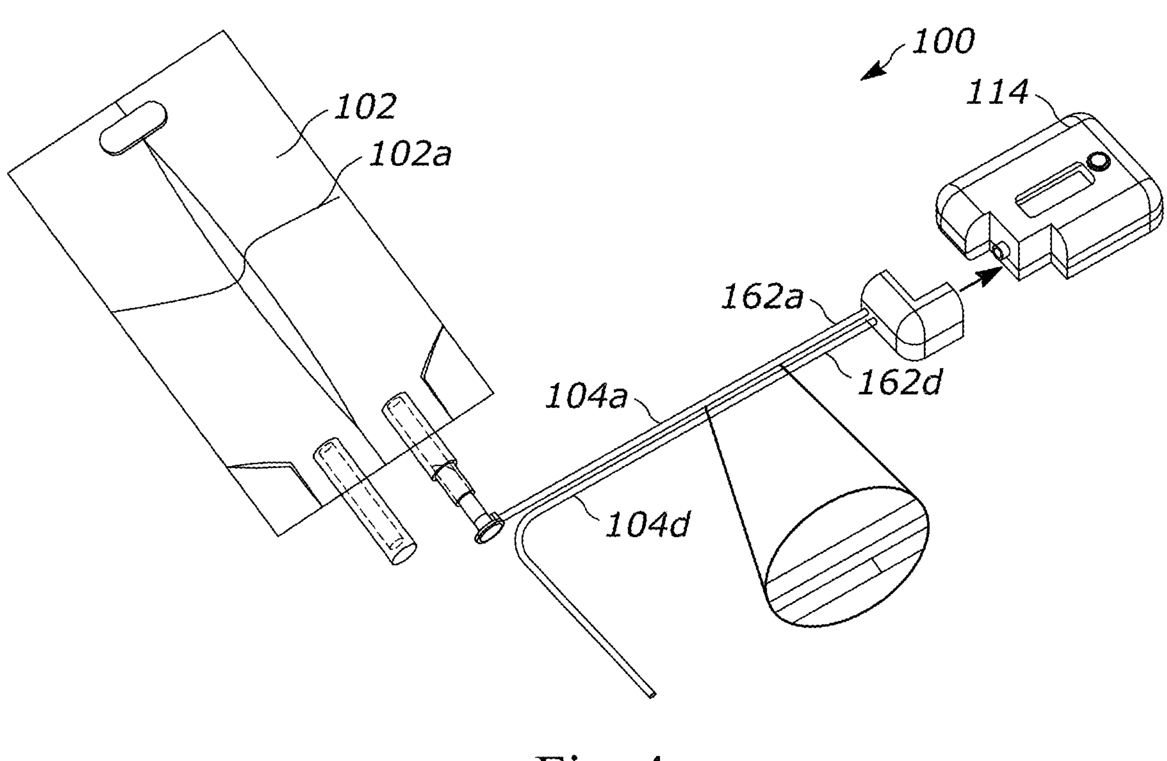
FIG. 4 illustrates an example drug delivery system in accordance with various embodiments.
FIG. 5 illustrates an example double gap flow cell in accordance with various embodiments.

FIG. 3 further shows an exploded view of the drive assembly 140 (e.g., the motor assembly), a tube set, and pressure sensors 150. With reference to FIGS. 3 and 4, the drive assembly 140 generally includes a motor 142, a retainer ring 143, an eccentric hub 144, a sleeve bearing 145, a pump race 146, an encoder board 147, and a generally pliant/flexible isolation mount or mounts 148. The motor 142 provides a rotational driving force. The retainer ring 143 retains other components in the housing (namely the tubes, as discussed more below) and/or for aligning the eccentric hub 144. The eccentric hub 144 utilizes a cam feature to generate peristalsis. The sleeve bearing 145 provides a barrier between the eccentric hub 144 and the tubing (such as the ring tube 158). The pump race 146 is adapted to house the previously-described circular shaped tube section. The encoder board 147 is configured to measure an actual speed of the motor for increased accuracy and precision. The generally pliant/flexible isolation mounts 148 prevent part misalignment, reduce drive torque/power, and provide compliance for head installation.

As illustrated in FIG. 4, an example drug delivery assembly 100 (or "system") is provided that may use the hand-held device 120. For example, the drug delivery assembly 100 includes a drug product container 102 for containing a drug product 102*a* (or medicament), an IV input line 104*a*, an IV output line 104*d*, each of which being in the form of the tubing portions 162*a*, 162*d* leading to and from the pump 114, The tubing portion 162*d* is coupled with the user via any number of suitable approaches such as, for example, an IV needle or cannula. In some examples, the pump 114 may be worn by and/or otherwise coupled with the user.

In some examples, a surface zeta-potential analytical method may be used to better understand the unique surface interactions between the molecules and the materials present within a given IV-bag system. This assessment may provide an optimized IVSS formulation so that a wide range of commercially available plastic materials may be utilized in healthcare facilities. In these approaches, streaming zeta-potential measurements may be used to obtain the surface zeta-potential for an IV-bag 102 and administration-line tubing materials 162 (as well as filters, CSTDs etc) (Anton Paar Surpass3). Also, an optimal concentration of IV-Bag Stabilizing Solution (IVSS) may be determined to passivate the surface material. Subsequently, the prevalence of a given BiTE®/protein to adsorb may be compared with different IV-bag material surfaces. As illustrated in FIG. 5, a double gap flow cell is illustrated to provide a miniaturized representation of an IV bag 104 having top and bottom layers and a flow path for the solution to flow therebetween.

Figure 7:
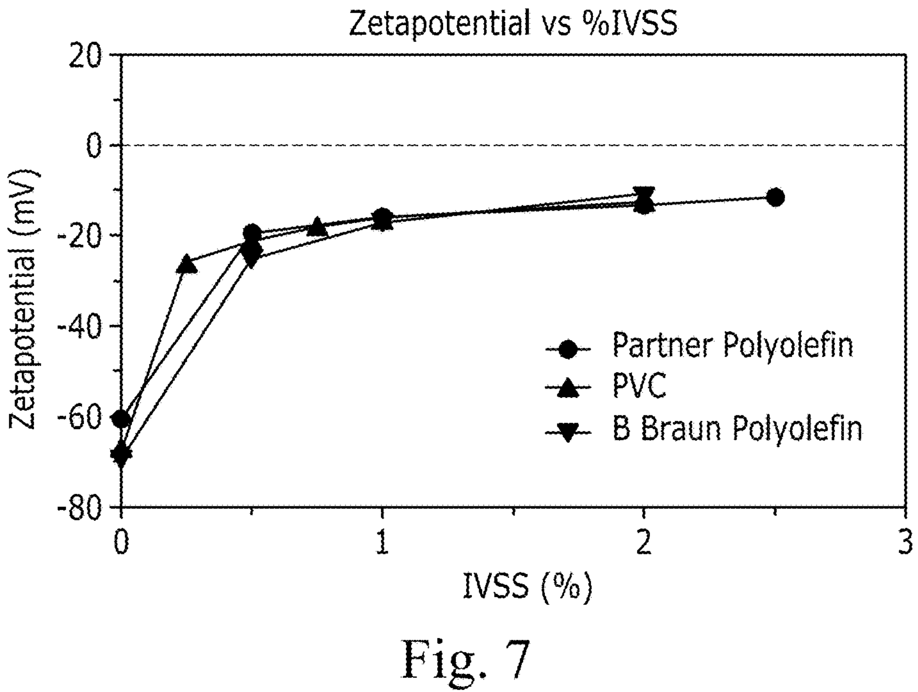
FIG. 7 illustrates an example zeta-potential analysis as a function of IVSS concentration in accordance with various embodiments.

The surface zeta potential is the potential drop across the mobile part of the double-layer and related to the surface charge at a solid/liquid interface. If negative charges are adsorbed at the surface of the material (i.e., the IV bag 102 and/or the tubing 162), the surface zeta potential is negative and vice-versa. Therefore, surface zeta potential may be used to determine whether the molecules will adsorb onto the IV bag 102 and/or tubing materials 162. As illustrated in FIG. 7, which measures the impact on zeta-potential when increasing the percentage of IVSS, upon adding IVSS, the zeta-potential increases by approximately 40 mV. The zeta-potential plateaus at approximately 1% IVSS. In some other examples, zeta potential may be measured by applying a known electric field to determine the electrophoretic mobility of the particles.

Figure 8:
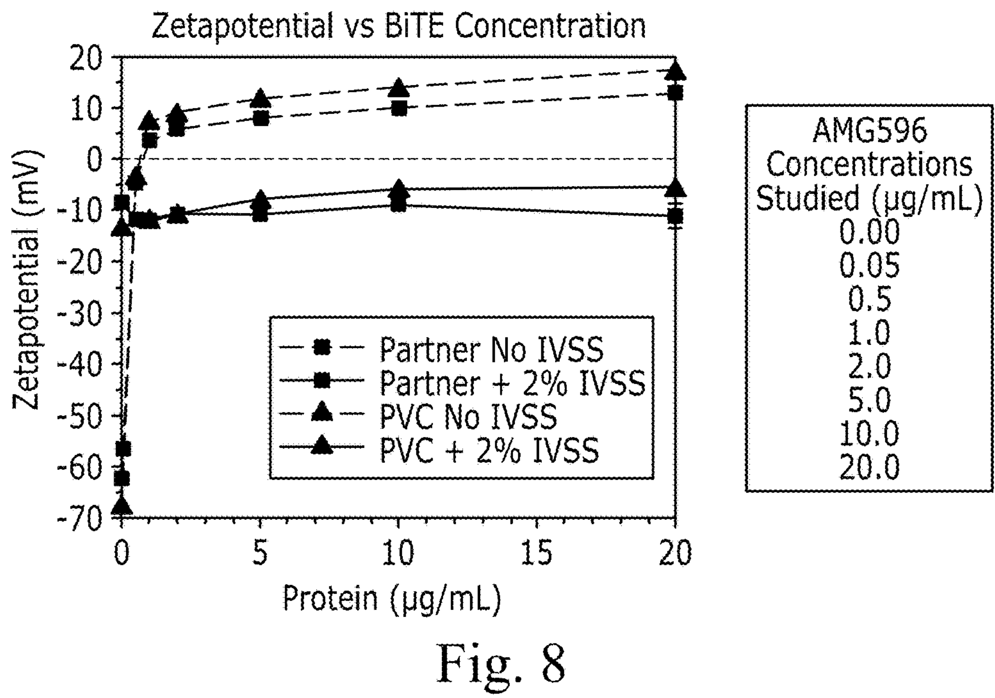
FIG. 8 illustrates an example zeta-potential analysis as a function of BiTE® concentration in accordance with various embodiments.

With reference to FIG. 8, zeta-potential analysis may be used to determine the effect of BiTE® concentrations on adsorption into different materials. More specifically, in the illustrated FIG. 8, different concentrations of AMG 596, an anti-EGFRvIll/CD3 BiTE® antibody were observed. A substantial difference in IVSS protection against adsorption on polyolefin IV-Bag films is shown as compared to a common alternative, polyvinyl chloride (PVC). Accordingly, a drug delivery system 100 for use with AMG 596 may incorporate a 2% IVSS solution for use with polyolefin IV-bags 102 while preventing adsorption. The zeta-potential of the molecules may be compared by varying the material the molecule flows through (e.g., EVA, polypropylene, polyurethane, etc.) while also varying an amount of IVSS added to the molecule to form a solution including the drug product.

Accordingly, by using zeta-potential analysis, it may be easier to determine if the IVSS is effective for different types of plastic chemistries and additionally, preferred materials for the IV-delivery of a group of drug products (e.g., to help with material selection) may be determined. The above techniques and results may provide the information necessary to optimize the IVSS formulation, potentially in a molecule-specific manner, so that a wide range of commercially available plastic materials can be utilized in clinics worldwide. Further, Pre-incubation with 2% IVSS addition prevents BiTE® adsorbtion and polyolefin material adsorbs measurably less BiTE® than PVC material (with or without IVSS present). This information may be of particular importance to address any number of the following potential issues: plasticizers are material specific and may affect stability (DEHP/TOTM); Barrier efficacy may be a consideration for long-term storage (extended holds and continuous infusion); regional differences in material preference/permitted use; material types may impact module recovery; leachable/extractable profiles may differ.

Additional BiTE® molecules and suitable system 100 materials will now be discussed. In a first alternative, a B-cell maturation antigen Half-life extended Bispecific T-Cell Engager (BCMA-HLE BiTE®; AMG 701) may be used in the system 100. In this example, the drug was determined to be physically stable in a 0.9% saline solution with 2% IVSS for intravenous administration and is compatible with ethylvinyl acetate (EVA) and/or polyolefin IV bags 102 as well as polyethylene and polyurethane (PU) infusion sets (i.e., tubing 162) both with and without 0.22 μm in-line filters. Further, the zeta-potential analysis determined that disposable plastic syringes may also be used. Further, tubing 162 constructed from PVC may be used for concentrations of AMG 701 of 25 μg/mL or more. At concentrations of 0.1 μg/mL and below, protein losses due to adsorption is higher than for other material types.

In order to prepare AMG 701 for intravenous infusion, IVSS is added to an IV bag 102 containing 0.9% sodium chloride at a 1:50 dilution. The lyophilized drug product 102*a* is reconstituted with 1.2 mL of sterile water for injection (SWFI) and the appropriate amount is then transferred into the IV bag 102 for dose preparation. The compatibility of AMG 701 with IVSS at 2% (1:50 dilution) in 0.9% saline was tested in IV bags 102 constructed from ethylene vinyl acetate and polyolefin as well as siliconized disposable syringes and polyethylene (PE), polyvinyl chloride (PVC), and polyurethane (PU) IV infusion sets (which includes tubing 162). Further, compatibility with 0.22 μm in-line filters was observed. As previously noted, AMG 701 maintains stability and potency after storage in EVA and polyolefin IV bags 102 as well as siliconized disposable syringes, and is compatible with PE and PU infusion sets with or without 0.22 μm filters. Further, the use of PVC infusion sets resulted in decreased protein concentrations.

A stability study using three concentrations was executed to support the proposed clinical doses between 2 μg/dose and 6500 μg/dose. More specifically, a low protein concentration of 0.1 μg/mL, an intermediate concentration of 25 μg/mL, and a high protein concentration of 100 μg/mL was executed. Further, ethylene vinyl acetate IV bags, polyolefin IV bags, disposable 20 mL syringes, polyolefin infusions sets, and PVC infusion sets (with and without 0.22 μm filters) and needles/catheters were tested for each concentration.

TABLE 1

List of IV administration containers and AMG 701 concentrations

| Container (nominal volume) | Concentration of AMG 701 (μg/mL) | Contact time (h) | Temperature (° C.) | Infusion set | Infusion rate (mL/h) |
|---|---|---|---|---|---|
| EVA IV bag | 100 | 0 | 5, 25 | PE (w/o filter) | uncontrolled |
| (100 mL) | | 24 | 5 | PE (w/o filter) | Uncontrolled |
| | | 24 | 25 | PE (with filter), PVC | 27 |
| EVA IV bag | 25 | 0 | 5, 25 | PE (w/o filter) | uncontrolled |
| (100 mL) | | 24 | 5 | PE (w/o filter) | Uncontrolled |
| | | 24 | 25 | PE (with filter), PVC | 27 |
| EVA IV bag | 0.1 | 0 | 5, 25 | PE (w/o filter) | uncontrolled |
| (100 mL) | | 24 | 5 | PE (w/o filter) | uncontrolled |
| | | 3 | 25 | PE (with, w/o filter) | uncontrolled |
| | | 4 | 25 | No infusion | n/a |
| | | 7, 24 | 25 | PE (with filter), PVC | 27 |
| Polyolefin IV bag | 100 | 0 | 5, 25 | PE (w/o filter) | uncontrolled |
| (100 mL) | | 24 | 5 | PE (w/o filter) | uncontrolled |
| | | 24 | 25 | PE (with filter), PVC | 27 |
| | | 24 | 25 | PU (w/o filter) | 27 |
| Polyolefin IV bag | 25 | 0 | 5, 25 | PE (w/o filter) | uncontrolled |
| (100 mL) | | 24 | 5 | PE (w/o filter) | uncontrolled |
| | | 24 | 25 | PE (with filter), PVC | 27 |
| | 0.1 | 0 | 5, 25 | PE (w/o filter) | Uncontrolled |
| Polyolefin IV bag | | 24 | 5 | PE (w/o filter) | Uncontrolled |
| (100 mL) | | 3 | 25 | PE (with filter) | Uncontrolled |
| | | 4 | 25 | No infusion | Uncontrolled |
| | | 7, 24 | 25 | PE (with filter), PVC | 27 |
| | | 24 | 25 | PU (w/o filter) | 27 |
| Syringe (20 mL) | 0.1 | 0, 24 | 5, 25 | PE (w/o filter) | 4 |

A visual inspection and subvisible particle analysis were used to determine physical stability of the drug product 102*a* in the IV bag 102 and disposable syringe. Size exclusion chromatography was used to test the amount of high molecular weight (HMW) protein species in the IV bag 102 and disposable syringe. A SPR binding assay was used to measure the concentration of drug product 102*a* in the IV bag 102 and disposable syringe. Samples were also tested with a binding assay (potency). Visual inspection results for AMG 701 in the IV administration containers demonstrate that the samples are practically free of visible particles.

Subvisible particles were measured using a light obscuration instrument. The number of subvisible particles remained below the USP and PhEur limits of particular matter (i.e., ≤6000 particles per container for ≥10 μm and ≤600 particles per container for 25 μm) for all concentrations in the 100 mL IV bags and the 20 mL disposable syringes (12 mL volume in 20 mL syringe) at all temperatures and time points with and without 0.22 μm inline filters (see FIG. 9)

Size exclusion chromatography with fluorescence detection was used to determine the high molecular weight (HMW) protein species in 25 μg/mL and 100 μm/mL samples. The relative area under the curve (AUC) attributed to HMW species of AMG 701 are provided in FIG. 10. The 0.1 μg/mL samples were not analyzed due to the low protein concentration. In summary AMG 701 was stable against the formation of HMW protein species under the tested conditions.

The protein concentration in the IV bags 102 and the disposable syringes was measured using a surface plasmon resonance (SPR) binding assay. The CD3 binding of the 0.1 μg/mL, 25 μg/mL, and 100 μg/mL samples was measured by SPR and the protein concentration estimated by comparison to a standard curve of solutions of AMG 701 of known protein concentration. The 25 μg/mL and 100 μg/mL solutions were first diluted to 0.1 μg/mL and measured by SPR.

Protein concentration in the IV bags and disposable syringes are summarized in FIGS. 11*a* and 11*b*. For samples with a nominal strength of 25 μg/mL and 100 μg/mL, the protein concentration did not change (≤±10%) over a 24 hour period in any of the IV administration containers and was at the same with (time 24 hours) and without (time 0 hour) the 0.22 μm inline filter in the IV administration set. These results indicate that there is no change in protein concentration in each of the IV administration containers.

For samples having a nominal length of 0.1 μg/mL, the protein concentration remained stable (e.g., <±10% change if compared to time 0 hr samples) for at least 24 hours storage at 2° C. to 8° C. or for at least four hours storage at 25° C. independent of the IV administration container. Protein concentration was also maintained during three hours of infusion through PE infusion sets equipped with 0.22 μm inline filter. The exposure of these samples to PVC infusion sets resulted in increased protein concentration losses (15-34%).

Binding assay (i.e., potency) results are summarized in FIG. 12. The 0.1 μg/mL samples were not analyzed due to low protein concentration. The results for 25 μg/mL and 100 μg/mL indicate that there are no significant differences between time 0 and time 24 hour samples as well as no significant difference between IV administration containers. All materials are stable and fully potent.

In a second alternative, a humanized bi-specific XmAb T cell recruiting antibody construct (AMG 424) is directed against a cluster of differentiation 3 (CD3) and cluster of differentiation 38 (CD38). The molecule includes three different protein chains: single chain variable fragment-constant fragment (scFv-Fc), heavy chain (HC), and light chain (LC). The scFv-Fc fragment antigen-binding (Fab) domain binds to the T-cell receptor associated CD3, while the HC and LC Fab domain binds to CD38. FIG. 13 illustrates the proposed structure of AMG 424. The illustrated scFv-Fc, HC, and LC subunits are covalently linked through ten intra-chain and three inter-chain disulfide bonds. The scFv-Fc and HC each contain an N-linked glycan at the consensus glycosylation site (NST) at asparagine 335 and 295, respectively. The scFv-Fc and HC glycosylation sites are illustrated as G1 and G2, respectively. AMG 424 includes 1144 amino acids. The amino acid sequences of scFv-Fc, HC, and LC are illustrated in FIG. 14. C-terminal lysine is mostly removed from the scFv-Fc and HC. The scFv-Fc is composed of 485 amino acids having a molecular mass of 52,613 Daltons (Da). The HC is composed of 445 amino acids with a molecular weight of 23,470 Da. The complete amino acid sequence of AMG 424 is verified through a combination of intact mass and liquid chromatography—mass spectrometry (LC-MS) of trypsin and HNE digested peptide mapping.

AMG 424 is supplied as a sterile, single use, preservative free lyophilized drug product to be reconstituted with sterile water for injection for IV infusion. Each single use vial includes 6.50 mg of AMG 424. The drug product 102*a* is formulated with 10 mM L-glutamic acid, 9% (w/v) sucrose, 0.01% polysorbate 80, pH 4.2. To prepare AMG 424 for IV infusion, IVSS is added to an infusion bag 102 containing 0.9% sodium chloride at a 1:20 dilution. The lyophilized drug product is reconstituted with 1.25 mL of sterile WFI and the appropriate amount is transferred into the infusion bag for dose preparation.

The compatibility of AMG 424 with IVSS at 5% (1:20 dilution) in 0.9% saline was tested in IV bags 102 constructed from polyolefin and ethyl vinyl acetate along with IV infusion sets having 0.22 μm filters. To summarize, AMG 424 maintained stability after storage in all containers for up to 24 hours at 2° C. to 8° C. and 25° C. The protein concentration of AMG 424 high dose samples (4 mg/mL) were determined using UV-Visible light spectroscopy. The protein concentration of AMG 424 low dose (1 μg/mL) samples were below the limit of detection for the UV-Visible Light Spectroscopy method. Accordingly, RP-UHPLC was used to determine concentration for these samples. The separation of AMG 424 from other impurities was achieved using a C8 column. A standard curve of the RP-UHPLC total integrated peak area was created from a set of AMG 424 solutions at low concentrations. The standard curve was then used to estimate the concentration of protein present in the unknown sample.

The test is performed to enumerate subvisible particles within specific size ranges. The apparatus used to test AMG 424 is an electronic, liquid-borne particle counting system that uses a light obscuration sensor along with a suitable sample-feeding device. Four aliquots (not less than 1 mL each) from a pool solution with a total volume of not less than 5 mL are degassed via a vacuum and analyzed. Data from the first aliquot is discarded and the number of particulates per container is calculated from the average of the remaining three measurements. Results are reported as the number of particles per container for particle sizes ≥10 μm and ≥25 μm. Additionally, particles ≥2 μm and ≥5 μm in size per container are monitored. The method is compliant with USP 787 and considered appropriate for AMG 424 as its intended use is specific to therapeutic proteins.

To determine compatibility with different IV infusion delivery materials, a stability study using two concentrations—a low protein concentration of 1 μg/mL and high protein concentration of 4 mg/mL—was executed to cover the proposed clinical doses between 50 μg/dose and 200 mg/dose. To cover a representative range of commonly used materials, EVA IV bags, polyolefin IV bags, polyolefin infusions sets (both with and without 0.22 μm filters) and needles/catheters were tested for each concentration (see FIG. 15). Visual inspection and subvisible particle analysis were used to determine physical stability of the drug product in the IV bag and disposable syringe. FIG. 16 illustrates the visual inspection results for AMG 424 in the IV container 102. In summary, the visual inspection determined that the samples are practically free of visible particles.

Subvisible particles were measured using a light obscuration instrument. The number of subvisible particles remained below the USP and PhEur limits for particulate matter (i.e., ≤6,000 particles per container for ≥10 μm and ≤600 particles per container for ≥25 μm) for both concentrations in the 250 mL IV bags at all temperatures and time points with and without 0.22 μm inline filters (see FIG. 17).

As illustrated in FIG. 18, the protein concentration was measured by RP-UHPLC and UV-Visible light spectroscopy assays. After admixing the AMG 424 concentration in each bag of the IV administration container 102 was analyzed by RP-UHPLC or UV-Visible light spectroscopy depending on sample concentration. The protein concentration recovery for the low dose was based on comparison of the RP-UHPLC total peak area of the unknown to a standard curve. UV-Visible light spectroscopy measured the protein concentration recovery of the high dose. The protein concentration did not change (±10%) over a 24 hour period in any of the IV administration containers and was the same with (t=24 h) and without (t=0) the 0.22 μm inline filter in the IV administration set. These results indicate that there is no change in protein concentration in each of the IV administration containers.

In summary, AMG 424 is physically stable in 0.9% saline with 5% IVSS for intravenous administration and is compatible with EVA and polyolefin IV bags and tubing materials used during product administration.

In a third alternative, material compatibility with a prostate-specific membrane antigen half-life extended bispecific T-Cell engager (PMSA-HLE BiTE®; AMG 160) is determined. In summary, AMG 160 is physically stable in 0.9% saline with 5% IVSS for intravenous administration and is compatible with EVA or polyolefin IV bags and polyethylene and polyurethane infusion sets with and without 0.22 μm in-line filters as well as disposable plastic syringes. To prepare AMG 160 for IV infusion, IVSS is added to the infusion bag 102 containing 0.9% sodium chloride at a 1:20 dilution. The lyophilized drug product is reconstituted with 1.2 mL of sterile WFI and the appropriate amount is transferred into the infusion bag for dose preparation.

To determine compatibility with different IV infusion delivery materials, a stability study using two concentrations—a low protein concentration of 0.1 μg/mL and high protein concentration of 62.5 mg/mL—was executed to cover the proposed clinical doses. To cover a representative range of commonly used materials, EVA IV bags, polyolefin IV bags, disposable syringes (20 mL), PE, PVC, and/or PU infusions sets (both with and without 0.22 μm filters) and needles/catheters were tested for each concentration (see FIG. 19). Appearance and subvisible particle analysis were used to determine physical stability of the drug product in the IV bag and disposable syringe. More specifically, SE-UHPLC was used to test the amount of high molecular weight (HMW) protein species as well as the concentration of the drug product in IV bags and disposable syringes. A SPR binding assay was used as an orthogonal method to analyze the concentration of drug product in IV bags and disposable syringes. Samples at 62.5 μg/mL were also tested with a binding assay (potency). Appearance results for AMG 160 in the IV administration container are summarized in FIG. 20. In summary, the visual inspection determined that the samples are practically free of visible particles.

Subvisible particles were measured using a light obscuration instrument. The number of subvisible particles remained below the USP and PhEur limits for particulate matter (i.e., ≤6,000 particles per container for ≥10 μm and ≤600 particles per container for ≥25 μm) for all samples (see FIGS. 21*a* & *b*).

With reference to FIGS. 22 & 23, SE-UHPLC with fluorescence detection was used to determine the HMW protein species in 62.5 μg/mL samples. The 0.1 μg/mL samples were not analyzed due to the low protein concentration. In summary, AMG 160 was stable against the formulation of HMW protein species under the tested conditions indicated by amounts remaining below 1% (FIG. 22). Further, SE-UHPLC with fluorescence detection was used to determine the concentration of the drug product in IV bags prior to and after infusion. The 0.1 μg/mL samples were again not analyzed due to the low protein concentration. Protein concentration for each sample was calculated from the respective area under the curve (AUC) using linear regression of a standard curve derived from AMG 160 solutions of known concentrations. Protein concentration in the IV bags are summarized in FIG. 23.

With reference to FIG. 24, the protein concentration in the IV bags and the disposable syringes was also measured using a surface plasmon resonance binding assay as an orthogonal method. The CD3 binding of the 0.1 μg/mL and 62.5 μg/mL samples were measured by SPR and the protein concentration estimated by comparison to a standard curve of solutions of AMG 160 of known protein concentration. The 62.5 μg/mL solutions were first diluted to 0.1 μg/mL and measured by SPR. Protein concentration in the IV bags and disposable syringes are summarized in FIG. 24. For samples with a nominal strength of 0.1 μg/mL, the protein concentration did not change ≤±6%) over a 24 hour period in any of the IV administration containers. Protein concentration also remained stable during infusion and when the solution passed a 0.22 μm in-line filter. For samples with a nominal strength of 62.5 μg/mL, the protein concentration did not change (≤±6%) over a 24 hour period in any of the IV administration containers. Protein concentration also remained stable during infusion and when the solution passed a 0.22 μm in-line filter. Accordingly, there is no change in protein concentration in each of the IV administration containers.

Binding assay (potency) results are provided in FIG. 25. The 0.1 μg/mL samples were again not analyzed due to the low protein concentration. The results for 62.5 μg/mL indicate that there are no significant differences between time 0 and time 24 hours samples as well as no significant difference between IV administration containers. The results indicate that AMG 160 remained stable and fully potent under tested conditions.

To summarize, AMG 160 is physically stable in 0.9% saline with 5% IVSS for IV administration and is compatible with EVA and polyolefin IV bags, PE, PVC, and PU infusion sets (with and without 0.22 μm in-line filters) as well as disposable plastic (polypropylene) syringes used during product administration.

In a fourth alternative, material compatibility with an HLE CD19-targeting BiTE® (AMG 562) is determined. To prepare AMG 562 for infusion, IVSS is added to infusion components containing 0.9% sodium chloride at a 1:20 dilution. The lyophilized drug product is reconstituted with 1.2 mL of sterile WFI and the appropriate amount is transferred into the infusion bag for dose preparation. The compatibility of AMG 562 drug product with IVSS at 5% (1:20 dilution) in 0.9% saline was tested in commonly used IV administration materials (EVA and polyolefin) and siliconized disposable syringes along with IV infusion sets and 0.22 μm in-line filters. The results demonstrated that AMG 562 maintained stability, and was fully recoverable and potent after storage in IV administration components for up to 24 hours at 25° C. A Protein A column was used to bind and elute AMG 562. The protein eluted as a single peak. The total protein loaded was determined by comparing the area under the curve to a known concentration curve.

To determine compatibility with different IV infusion delivery materials, a stability study using two concentrations—a low protein concentration of 50 ng/mL and high protein concentration of 10 μg/mL—was executed to cover the proposed clinical doses between 100 ng/dose and 1 mg/dose. AMG 562 was prepared with 5% IVSS in the IV administration materials (EVA and polyolefin) and disposable syringes for up to 24 hours at 25° C. (see FIG. 26). Negative controls without IVSS were added to both IV bag types at the lowest protein concentration to demonstrate the effectiveness of 5% IVSS to eliminate protein loss. Samples were taken directly from the IV bag at time zero. After 24 hours, a second sample was taken after flowing through the infusion line and filter.

After preparation and storage of AMG 562 in the described IV administration materials, the protein concentration of the 50 ng/mL and 10 μg/mL samples were analyzed by affinity Protein A HPLC chromatography and compared to the concentration at time zero to determine if any loss occurred due to adsorption to surfaces. After storage for 24 hours at 25° C. (FIG. 27), no significant losses in AMG 562 with 5% IVSS at 50 ng/mL and 10 μg/mL were observed. The protein loss was significant in AMG 562 without IVSS at 50 ng/mL, demonstrating the need for the addition of 5% IVSS to the IV infusion materials.

With reference to FIGS. 28-30, aggregation was monitored using SE-UHPLC. The results for SE-UHPLC showed no change in percent HMW species at 10 μg/mL (FIG. 28). The 50 ng/mL AMG 562 concentration was below the level of quantitation for the SE-UHPLC assay. Accordingly, the results from the 10 μg/mL AMG 562 are expected to be representative of the lower concentration. The subvisible particle counts was quantified using HIAC (i.e., a light obscuration instrument), and visual analysis was used to determine visible particles were present in both 50 ng/mL and 10 μg/mL concentrations. The subvisible particle counts were at or below 18 particles per mL at the size of 10 μm or greater and at or below 2 particle per mL at the 25 μm size or greater (FIG. 29). The results from visual inspection demonstrate that IV administration materials (EVA and polyolefin) and siliconized disposable syringes are practically free of visible particles.

The percent relative potency results showed no change in potency at 10 μg/mL (FIG. 30). The 50 ng/mL samples were not analyzed due to the low protein concentration. Thus, the results from the 10 μg/mL AMG 562 are expected to be representative of the lower concentration.

Based on the SE-UHPLC, subvisible, and visible particle data, and potency results, AMG 562 was compatible with siliconized disposable syringes, IV bags constructed from EVA or polyolefin, and remained physically stable and potent for the duration of the testing in 0.9% saline with 5% IVSS.

In a fifth alternative, material compatibility with AMG 757 is determined. To prepare AMG 757 for infusion, IVSS is added to infusion components containing 0.9% sodium chloride at a 1:20 dilution. The lyophilized drug product is reconstituted with 1.2 mL of sterile WFI and the appropriate amount is transferred into the infusion bag for dose preparation. The compatibility of AMG 757 drug product with IVSS at 5% (1:20 dilution) in 0.9% saline was tested in commonly used IV administration materials (EVA and polyolefin) and siliconized disposable syringes along with IV infusion sets with 0.22 μm in-line filters. The results demonstrated that AMG 757 maintained stability, and was fully potent after storage in all containers for up to 24 hours at 2° C. to 8° C. and 25° C. A SE-UHPLC assay was used to estimate protein recovery. A standard curve of the SE-UHPLC total integrated peak area was created from a set of AMG 757 solutions at known concentrations. The standard curve was then used to estimate the concentration of protein present in the unknown sample.

To determine compatibility with different IV infusion delivery materials, a stability study using two concentrations—a low protein concentration of 20 μg/mL and high protein concentration of 1 mg/mL—was executed to cover the proposed clinical doses between 3 μg/dose and 100 mg/dose. To cover a representative range of commonly used materials, EVA and polyolefin IV bags, disposable syringes (60 cc), polyolefin infusion sets with and without 0.22 μm filters, and needles/catheters were tested for each concentration. FIG. 31 details the tested configurations.

Visual inspection and subvisible particle analysis were used to determine physical stability of the drug product in the IV bag and disposable syringe. A SE-UHPLC assay was used to measure the concentration of drug product in the IV bag. Samples were also tested with a cell-based bioassay (potency). FIG. 32 illustrates the visual inspection results for AMG 757 in the IV container 102. In summary, the visual inspection determined that the samples are practically free of visible particles.

Subvisible particles were measured using a light obscuration instrument. The number of subvisible particles remained below the USP and PhEur limits of particular matter (i.e., ≤6000 particles per container for 10 μm and ≤600 particles per container for 25 μm) for both concentrations in the 100 mL IV bags and the 60 cc disposable syringes (50 mL volume in 60 cc syringe) at all temperatures and time points with and without 0.22 μm inline filters (see FIG. 33).

With reference to FIG. 34, the SE-UHPLC assay percent recovery measurements are summarized. After admixing, the AMG 757 concentration in each of the IV administration containers was analyzed. The percent recovery was based on comparison of the SE-UHPLC total peak area of the unknown to a standard curve. The protein concentration did not change (±10%) over a 24 hour period in any of the IV administration containers and was the same with (t=24 h) and without (t=0 and t=4 h) the 0.22 μm inline filter in the IV administration set. These results indicate that there is no change in protein concentration in each of the IV administration containers.

With reference to FIG. 35, cell-based bioassay (potency) results are summarized and indicate that there are no significant differences between t=0 and t=24 h samples as well as no significant differences between IV administration containers. The results indicate that all materials are stable and are fully potent. To summarize, AMG 757 is physically stable in 0.9% saline with 5% IVSS for intravenous administration and is compatible with EVA and polyolefin IV bags, tubing materials, as well as disposable plastic syringes used during product administration.

In some examples, the IVSS may include polysorbate. In some examples, the IVSS formulation may include approximately 1.25 M lysine monohydrocholoride, 25 mM citric acid monohydrate, 0.1% (w/v) polysorbate 80, and has a pH of approximately 7.0. In other examples, the IVSS 54 may include similar formulations, but also have a minimum of approximately 0.9% NaCl and approximately 0.001 to approximately 0.1% (w/v) polysorbate 80. It is appreciated that different BiTE® require different final percentages of IVSS 54 in the delivery container. This percentage may vary between approximately 0.5% to approximately 12% of the final volume in the delivery container. Further, citrate may increase the risk of glass delamination if filled in glass vials. In the event that citrate is necessary for drug product stabilization (determined on a per-product basis), the delivery containers may be constructed from CZ or other plastic compositions. Other examples of ingredients for suitable IVSSs 54 are possible. Suitable IVSS 54 concentrations protect against protein-plastic interactions and/or surface adsorption, and more specifically, in the lower end of the concentration range where even minor losses may potentially change the effective dose. The below table illustrates example component concentrations for varying IVSS concentrations:

TABLE 2

Component Concentrations with Varying IVSS Concentrations (top column units are (V/v) % of IVSS

| IVSS COMPONENTS | 0.5 | 1.0 | 2.0 | 4.0 | 6.0 | 8.0 | 10.0 | 12.0 |
|---|---|---|---|---|---|---|---|---|
| Lysine monohydrochloride (M) | 0.00625 | 0.0125 | 0.025 | 0.05 | 0.075 | 0.1 | 0.125 | 0.15 |
| Citrate Monohydrate (M) | 0.000125 | 0.00025 | 0.0005 | 0.001 | 0.0015 | 0.002 | 0.0025 | 0.003 |
| Polysorbate 80 (% w/v) | 0.0005 | 0.001 | 0.002 | 0.004 | 0.006 | 0.008 | 0.01 | 0.012 |

The drug product container may be in the form of an IV bag, a vial, a prefilled syringe, or similar container that includes a reconstitution container body defining an inner volume. The inner volume may be sterile. In some approaches, the reconstitution container adapter may also be a CSTD (or, in examples where the prefilled reconstitution container is in the form of a syringe, the container adapter may be a needle) that mates, engages, and/or couples to the vial adapter. Additionally or alternatively, the drug product can be bulk lyophilized and filled into a cartridge or container that is typically used to administer with an IV pump. If needed the dehydrated forms of IVSS, NaCl, and any other components needed for the final administered solution can be bulk lyophilized and filled into the cassette for long term storage.

As previously noted, in some examples, the prefilled drug product container may be in the form of a prefilled syringe that contains the drug product. In these examples the drug product may be in the form of a liquid BiTE® formulation used in conjunction with a monoclonal antibody (mAb), In these examples, the drug product may be directly added to the delivery container without the use of a vial adapter system (such as the above-mentioned CSTDs) where more traditional needle-syringe injection/delivery into the container is preferred, which may advantageously simplify and/or improve supply chain and manufacturing control, and may further allow for more compact commercial packaging that takes up less space in storage systems at healthcare facilities. In these examples, the prefilled drug product vial may or may not need to be reconstituted prior to transferring the drug product to the delivery container.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β37 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM; LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP Ilb/Ilia receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40 L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-(R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfony)pethyl]-2,3-dihydro-1,3-dioxo-1H-isoindo-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE®

(bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A method of determining material compatibility for components of a drug delivery system, including using a surface zeta-potential analytical method to evaluate surface interactions between a desired molecule and at least one material present within a given IV-bag system, wherein the at least one material comprises a first potential material, the method further comprising the steps of:

providing a double gap flow cell having a top layer, a bottom layer, and a flow path for the desired molecule to flow therebetween in the given IV-bag system, the top and bottom layers being constructed from the first potential material;

measuring a first zeta-potential of the given IV-bag system when the desired molecule flows through the first potential material of the top layer and the first potential material of the bottom layer.

2. The method of claim 1, further comprising the steps of:

replacing the first potential material with a second potential material;

measuring a second zeta-potential when the given IV-bag system flows through the second potential material of the top layer and the second potential material of the bottom layer; and comparing the first zeta-potential with the second zeta-potential.

3. The method of claim 1, wherein the desired molecule includes a drug product to be delivered intravenously.

4. The method of claim 3, further comprising the step of forming a solution with the drug product and an intravenous solution stabilizer and measuring a zeta-potential of the solution.

* * * * *